United States Patent
Khair et al.

(10) Patent No.: US 6,897,788 B2
(45) Date of Patent: May 24, 2005

(54) WIRELESS SYSTEM PROTOCOL FOR TELEMETRY MONITORING

(75) Inventors: Mohammad Khair, Hoffman Estates, IL (US); Salvador Lopez, Park Ridge, IL (US); Richard Ng, Cary, IL (US); Sanjar Ghaem, Chesapeake, VA (US); William L. Olson, Lake Villa, IL (US)

(73) Assignee: Motorola, Inc., Schaumburg, IL (US)

( * ) Notice: Subject to any disclaimer, the term of this patent is extended or adjusted under 35 U.S.C. 154(b) by 370 days.

(21) Appl. No.: 10/124,679

(22) Filed: Apr. 17, 2002

(65) Prior Publication Data

US 2002/0109621 A1 Aug. 15, 2002

Related U.S. Application Data

(62) Division of application No. 09/551,719, filed on Apr. 18, 2000, now Pat. No. 6,441,747.

(51) Int. Cl.[7] .............................................. G08B 21/00
(52) U.S. Cl. ........................ 340/870.16; 340/870.11; 340/870.07; 607/30; 607/60; 607/62; 128/903
(58) Field of Search ....................... 340/870.11, 870.16, 340/870.07; 128/903, 901; 607/30, 60, 62; 600/508, 509

(56) References Cited

U.S. PATENT DOCUMENTS

| | | | |
|---|---|---|---|
| 2,864,943 A | 12/1958 | Schultz | 250/15 |
| 2,958,781 A | 11/1960 | Marchal et al. | 250/83.3 |
| 3,199,508 A | 8/1965 | Roth | 128/2.06 |
| 3,495,584 A | 2/1970 | Schwalm | 128/2.06 |
| 3,602,215 A | 8/1971 | Parnell | 128/2.06 B |
| 3,603,881 A | 9/1971 | Thornton | 325/30 |
| 3,727,190 A | 4/1973 | Vogelman et al. | 340/172.5 |
| 3,729,708 A | 4/1973 | Wolfer et al. | 340/146.1 F |
| 3,757,778 A | 9/1973 | Graham | 128/2.06 R |
| 3,774,594 A | 11/1973 | Huszar | 128/2.06 R |
| 3,810,102 A | 5/1974 | Parks, III et al. | 340/172.5 |
| 3,830,228 A | 8/1974 | Foner | 128/2.06 R |

(Continued)

FOREIGN PATENT DOCUMENTS

| | | |
|---|---|---|
| EP | 0212278 | 3/1987 |
| GB | 2271691 | 4/1994 |
| WO | WO 97/49077 | 12/1997 |
| WO | WO 98/00056 | 1/1998 |

OTHER PUBLICATIONS

PCT Notification of Transmittal of the International Search Report or the Declaration.
Performance Specification sheet published for Motorola C.O.R. HT–220 Handie–Talkie FM Radio, printed 1973 by Motorola, 2 pages.
Performance Specification sheet published for Motorola C.O.R. HT–220 "Handie–Talkie" FM Radio, printed 1971 by Motorola, 2 pages.

*Primary Examiner*—Albert K Wong
(74) *Attorney, Agent, or Firm*—Brinks Hofer Gilson & Lione

(57) ABSTRACT

A wireless, programmable system for medical monitoring includes a base unit and a plurality of individual wireless, remotely programmable biosensor transceivers. The base unit manages the transceivers by issuing registration, configuration, data acquisition, and transmission commands using wireless techniques. Physiologic data from the wireless transceivers is demultiplexed and supplied via a standard interface to a conventional monitor for display. Initialization, configuration, registration, and management routines for the wireless transceivers and the base unit are also described.

39 Claims, 17 Drawing Sheets

U.S. PATENT DOCUMENTS

| | | |
|---|---|---|
| 3,834,373 A | 9/1974 | Sato .................. 128/2.06 E |
| 3,905,364 A | 9/1975 | Cudahy et al. ........ 128/2.06 R |
| 3,925,762 A | 12/1975 | Heitlinger et al. .......... 340/150 |
| 3,943,918 A | 3/1976 | Lewis ................ 128/2.1 A |
| 3,949,397 A | 4/1976 | Wagner et al. .......... 343/6.5 R |
| 3,970,996 A | 7/1976 | Yasaka et al. .......... 340/172.5 |
| 3,986,498 A | 10/1976 | Lewis ................ 128/2.06 R |
| 4,027,663 A | 6/1977 | Fischler et al. ........ 128/2.06 R |
| 4,042,906 A | 8/1977 | Ezell .................. 340/15.5 TS |
| 4,051,522 A | 9/1977 | Healy et al. ................ 358/86 |
| 4,074,228 A | 2/1978 | Jonscher ............ 340/146.1 AQ |
| 4,121,573 A | 10/1978 | Crovella et al. ........ 128/2.1 A |
| 4,124,894 A | 11/1978 | Vick et al. ................ 364/417 |
| 4,141,351 A | 2/1979 | James et al. .......... 128/2.06 R |
| 4,150,284 A | 4/1979 | Trenkler et al. ............ 250/199 |
| 4,156,867 A | 5/1979 | Bench et al. ............. 340/146.1 |
| 4,173,221 A | 11/1979 | McLaughlin et al. ....... 128/696 |
| 4,173,971 A | 11/1979 | Karz ........................ 128/702 |
| 4,186,749 A | 2/1980 | Fryer ........................ 128/748 |
| 4,216,462 A | 8/1980 | McGrath et al. ............ 340/150 |
| 4,233,241 A | 11/1980 | Kalopissis et al. .......... 564/221 |
| 4,237,900 A | 12/1980 | Schulman et al. .......... 128/630 |
| 4,260,951 A | 4/1981 | Lewyn ...................... 328/165 |
| 4,262,632 A | 4/1981 | Hanton et al. ................ 119/1 |
| 4,281,664 A | 8/1981 | Duggan ...................... 128/696 |
| 4,321,933 A | 3/1982 | Baessler .................... 128/736 |
| 4,353,372 A | 10/1982 | Ayer ........................ 128/640 |
| 4,396,906 A | 8/1983 | Weaver ................ 340/347 DD |
| 4,425,921 A | 1/1984 | Fujisaki et al. ............. 128/690 |
| 4,441,498 A | 4/1984 | Nordling ................ 128/419 P |
| 4,449,536 A | 5/1984 | Weaver .................. 128/696 |
| 4,471,786 A | 9/1984 | Inagaki et al. .............. 128/748 |
| 4,475,208 A | 10/1984 | Ricketts ........................ 375/1 |
| 4,510,495 A | 4/1985 | Sigrimis et al. ....... 340/825.54 |
| 4,521,918 A | 6/1985 | Challen ...................... 455/343 |
| 4,531,526 A | 7/1985 | Genest |
| 4,537,200 A | 8/1985 | Widrow ...................... 128/696 |
| 4,556,061 A | 12/1985 | Barreras et al. ........ 128/419 PT |
| 4,556,063 A | 12/1985 | Thompson et al. .... 128/419 PT |
| 4,562,840 A | 1/1986 | Batina et al. .......... 128/419 PT |
| 4,573,026 A | 2/1986 | Curtis et al. .................. 332/18 |
| 4,583,548 A | 4/1986 | Schmid ...................... 128/639 |
| 4,583,549 A | 4/1986 | Manoli ...................... 128/640 |
| 4,585,004 A | 4/1986 | Brownlee ............ 128/419 PT |
| 4,586,508 A | 5/1986 | Batina et al. .......... 128/419 PG |
| 4,598,281 A | 7/1986 | Maas ........................ 340/664 |
| 4,599,723 A | 7/1986 | Eck ............................ 371/47 |
| 4,601,043 A | 7/1986 | Hardt et al. ..................... 375/1 |
| 4,606,352 A | 8/1986 | Geddes et al. .............. 128/702 |
| 4,608,994 A | 9/1986 | Ozawa et al. |
| 4,618,861 A | 10/1986 | Gettens et al. .......... 340/825.54 |
| 4,625,733 A | 12/1986 | Saynajakangas ............ 128/687 |
| RE32,361 E | 2/1987 | Duggan ...................... 128/696 |
| 4,653,068 A | 3/1987 | Kadin .......................... 375/1 |
| 4,681,118 A | 7/1987 | Asai et al. .................. 128/643 |
| 4,709,704 A | 12/1987 | Lukasiewicz ............... 128/644 |
| 4,724,435 A | 2/1988 | Moses et al. .......... 340/870.13 |
| 4,747,413 A | 5/1988 | Bloch ........................ 128/736 |
| 4,754,483 A | 6/1988 | Weaver ........................ 381/36 |
| 4,783,844 A | 11/1988 | Higashiyama et al. ........ 455/34 |
| 4,784,162 A | 11/1988 | Ricks et al. ................ 128/903 |
| 4,791,933 A | 12/1988 | Asai et al. .................. 128/640 |
| 4,794,532 A | 12/1988 | Leckband et al. ..... 364/413.06 |
| 4,799,059 A | 1/1989 | Grindahl et al. ....... 340/870.03 |
| 4,802,222 A | 1/1989 | Weaver ........................ 381/35 |
| 4,803,625 A | 2/1989 | Fu et al. ................ 364/413.03 |
| 4,805,631 A | 2/1989 | Roi du Maroc, II ........ 128/710 |
| 4,835,372 A | 5/1989 | Gombrich et al. ........... 235/375 |
| 4,839,806 A | 6/1989 | Goldfischer et al. ... 364/413.02 |
| 4,850,009 A | 7/1989 | Zook et al. ................... 379/96 |
| 4,857,893 A | 8/1989 | Carroll |
| 4,860,759 A | 8/1989 | Kahn et al. .................. 128/668 |
| 4,865,044 A | 9/1989 | Wallace et al. ............. 128/736 |
| 4,883,064 A | 11/1989 | Olson et al. ................ 128/696 |
| 4,889,131 A | 12/1989 | Salem et al. ................ 128/671 |
| 4,889,132 A | 12/1989 | Hutcheson et al. ......... 128/680 |
| 4,907,248 A | 3/1990 | Bretl .......................... 375/27 |
| 4,909,260 A | 3/1990 | Salem et al. ................ 128/721 |
| 4,916,441 A | 4/1990 | Gombrich ................... 340/712 |
| 4,928,187 A | 5/1990 | Rees ........................... 360/40 |
| 4,955,075 A | 9/1990 | Anderson ................... 455/182 |
| 4,957,109 A | 9/1990 | Groeger et al. ............. 128/640 |
| 4,958,645 A | 9/1990 | Cadell et al. ............... 128/903 |
| 4,966,154 A | 10/1990 | Cooper et al. .............. 128/671 |
| 4,974,607 A | 12/1990 | Miwa ........................ 128/904 |
| 4,981,141 A | 1/1991 | Segalowitz |
| 5,012,411 A | 4/1991 | Policastro et al. ...... 364/413.06 |
| 5,025,452 A | 6/1991 | Sohner et al. ................. 375/1 |
| 5,025,808 A | 6/1991 | Hafner ...................... 128/696 |
| 5,036,462 A | 7/1991 | Kaufman et al. ....... 364/413.01 |
| 5,036,869 A | 8/1991 | Inahara ...................... 128/903 |
| 5,042,498 A | 8/1991 | Dukes ........................ 128/696 |
| 5,051,799 A | 9/1991 | Paul et al. .................... 375/25 |
| 5,072,383 A | 12/1991 | Brimm et al. .......... 364/413.02 |
| 5,077,753 A | 12/1991 | Grau ............................ 375/1 |
| 5,078,134 A | 1/1992 | Heilman et al. ............. 128/421 |
| 5,085,224 A | 2/1992 | Galen et al. ................ 128/696 |
| 5,109,845 A | 5/1992 | Yuuchi et al. ............... 128/421 |
| 5,113,869 A | 5/1992 | Nappholz et al. ........... 128/696 |
| 5,127,404 A | 7/1992 | Wyborny et al. ........ 128/419 P |
| 5,131,399 A | 7/1992 | Sciarra ...................... 128/671 |
| 5,137,022 A | 8/1992 | Henry .................. 128/419 PT |
| 5,153,584 A | 10/1992 | Engira |
| 5,157,604 A | 10/1992 | Axford et al. ......... 364/413.03 |
| 5,168,874 A | 12/1992 | Segalowitz |
| 5,171,977 A | 12/1992 | Morrison .................... 235/375 |
| 5,177,765 A | 1/1993 | Holland et al. ................ 375/1 |
| 5,177,766 A | 1/1993 | Holland et al. ................ 375/1 |
| 5,179,569 A | 1/1993 | Sawyer ........................ 375/1 |
| 5,179,571 A | 1/1993 | Schilling ........................ 375/1 |
| 5,181,519 A | 1/1993 | Bible .......................... 128/704 |
| 5,192,949 A | 3/1993 | Suzuki et al. .................. 341/68 |
| 5,205,294 A | 4/1993 | Flach et al. ................. 128/696 |
| 5,212,476 A | 5/1993 | Maloney ................ 340/825.19 |
| 5,212,715 A | 5/1993 | Pickert et al. ............... 375/114 |
| 5,224,485 A | 7/1993 | Powers et al. ............. 128/696 |
| 5,226,431 A | 7/1993 | Bible et al. .................. 128/904 |
| 5,238,001 A | 8/1993 | Gallant et al. ............... 128/700 |
| 5,270,811 A | 12/1993 | Ishibashi et al. ............. 358/108 |
| 5,272,477 A | 12/1993 | Tashmia et al. ........ 340/870.16 |
| 5,292,343 A | 3/1994 | Blanchette et al. ............ 607/32 |
| 5,305,202 A | 4/1994 | Gallant et al. ......... 364/413.06 |
| 5,305,353 A | 4/1994 | Weerackody ............... 375/100 |
| 5,307,372 A | 4/1994 | Sawyer et al. .................. 375/1 |
| 5,307,817 A | 5/1994 | Guggenbuhl et al. ........ 128/696 |
| 5,307,818 A | 5/1994 | Segalowitz |
| 5,309,920 A | 5/1994 | Gallant et al. ............... 128/710 |
| 5,314,450 A | 5/1994 | Thompson .................... 607/32 |
| 5,335,664 A | 8/1994 | Nagashima ................. 128/696 |
| 5,339,824 A | 8/1994 | Engira ....................... 128/712 |
| 5,342,408 A | 8/1994 | deCoriolis et al. ............ 607/32 |
| 5,343,869 A | 9/1994 | Pross et al. .................. 128/700 |
| 5,348,008 A | 9/1994 | Bornn et al. ................ 128/642 |
| 5,353,791 A | 10/1994 | Tamura et al. .............. 128/633 |
| 5,353,793 A | 10/1994 | Bornn ........................ 128/642 |
| 5,354,319 A | 10/1994 | Wyborny et al. .............. 607/32 |
| 5,359,641 A | 10/1994 | Schull et al. ................ 379/106 |
| 5,365,530 A | 11/1994 | Yoshida .................... 371/37.4 |
| 5,375,604 A | 12/1994 | Kelly et al. ................. 128/671 |
| 5,377,222 A | 12/1994 | Sanderford, Jr. ............... 375/1 |
| 5,381,798 A | 1/1995 | Burrows .................... 128/696 |

| | | | |
|---|---|---|---|
| 5,392,771 A | 2/1995 | Mock et al. ............ 128/205.23 |
| 5,394,879 A | 3/1995 | Gorman ................... 128/707 |
| 5,394,882 A | 3/1995 | Mawhinney ............... 128/721 |
| 5,400,794 A | 3/1995 | Gorman ................... 128/696 |
| 5,416,695 A | 5/1995 | Stutman et al. ........ 364/413.02 |
| 5,417,222 A | 5/1995 | Dempsey et al. ........... 128/696 |
| 5,438,329 A | 8/1995 | Gastouniotis et al. .. 340/870.02 |
| 5,438,607 A | 8/1995 | Przygoda, Jr. et al. ........ 379/38 |
| 5,441,047 A | 8/1995 | David et al. ................. 128/670 |
| 5,444,719 A | 8/1995 | Cox et al. ................... 371/37.1 |
| 5,458,122 A | 10/1995 | Hethuin |
| 5,458,123 A | 10/1995 | Unger ....................... 128/696 |
| 5,458,124 A | 10/1995 | Stanko et al. ............... 128/696 |
| 5,464,021 A | 11/1995 | Birnbaum ................. 128/696 |
| 5,485,848 A | 1/1996 | Jackson et al. ............. 128/672 |
| 5,491,474 A | 2/1996 | Suni et al. ............. 340/870.31 |
| 5,507,035 A | 4/1996 | Bantz et al. ................. 455/133 |
| 5,511,553 A | 4/1996 | Segalowitz |
| 5,522,396 A | 6/1996 | Langer et al. .............. 128/696 |
| 5,524,637 A | 6/1996 | Erickson ................... 128/779 |
| 5,538,007 A | 7/1996 | Gorman .................... 128/710 |
| 5,544,649 A | 8/1996 | David et al. ............... 128/630 |
| 5,544,661 A | 8/1996 | Davis et al. ............... 128/700 |
| 5,546,950 A | 8/1996 | Schoeckert et al. ......... 128/696 |
| 5,549,113 A | 8/1996 | Halleck et al. ............. 128/671 |
| 5,564,429 A | 10/1996 | Bornn et al. ................ 128/696 |
| 5,576,952 A | 11/1996 | Stutman et al. ........ 364/413.02 |
| 5,579,001 A | 11/1996 | Dempsey et al. ...... 340/870.01 |
| 5,579,378 A | 11/1996 | Arlinghaus, Jr. ............ 379/106 |
| 5,579,775 A | 12/1996 | Dempsey et al. ........... 128/670 |
| 5,579,781 A | 12/1996 | Cooke ........................ 128/733 |
| 5,582,180 A | 12/1996 | Manset et al. ............. 128/696 |
| 5,586,552 A | 12/1996 | Sakai .......................... 128/633 |
| 5,617,871 A | 4/1997 | Burrows .................... 128/696 |
| 5,628,324 A | 5/1997 | Sarbach ..................... 128/670 |
| 5,634,468 A | 6/1997 | Platt et al. .................. 128/696 |
| 5,640,953 A | 6/1997 | Bishop et al. .............. 128/630 |
| 5,646,701 A | 7/1997 | Duckworth et al. ... 340/825.69 |
| 5,664,270 A | 9/1997 | Bell et al. ....................... 5/600 |
| 5,678,545 A | 10/1997 | Stratbucker ................ 128/640 |
| 5,678,562 A | 10/1997 | Sellers ....................... 128/710 |
| 5,685,303 A | 11/1997 | Rollman et al. ............ 128/644 |
| 5,694,940 A | 12/1997 | Unger et al. ................ 128/696 |
| 5,704,351 A | 1/1998 | Mortara et al. ............. 128/630 |
| 5,718,234 A | 2/1998 | Warden et al. .............. 128/696 |
| 5,720,771 A | 2/1998 | Snell |
| 5,724,985 A | 3/1998 | Snell |
| 5,738,102 A | 4/1998 | Lemelson .................... 128/671 |
| 5,748,103 A | 5/1998 | Flach et al. ............ 340/870.07 |
| 5,755,230 A | 5/1998 | Schmidt et al. ............. 128/731 |
| 5,759,199 A | 6/1998 | Snell et al. ................... 607/60 |
| 5,767,791 A | 6/1998 | Stoop et al. ........... 340/870.11 |
| 5,779,630 A | 7/1998 | Fein et al. .................. 600/323 |
| 5,788,633 A | 8/1998 | Mahoney .................. 600/382 |
| 5,800,204 A | 9/1998 | Niitsu ....................... 439/495 |
| 5,813,404 A | 9/1998 | Devlin et al. .............. 128/639 |
| 5,819,740 A | 10/1998 | Muhlenberg ............... 128/696 |
| 5,820,567 A | 10/1998 | Mackie ...................... 600/519 |
| 5,827,179 A | 10/1998 | Lichter et al. ............. 600/300 |
| 5,862,803 A | 1/1999 | Besson et al. |
| 5,865,733 A | 2/1999 | Malinouskas et al. ...... 600/300 |
| 5,868,671 A | 2/1999 | Mahoney .................. 600/382 |
| 5,871,451 A | 2/1999 | Unger et al. ............... 600/509 |
| 5,873,369 A | 2/1999 | Laniado et al. ............ 128/903 |
| 5,882,300 A | 3/1999 | Malinouskas et al. ...... 600/300 |
| 5,899,928 A | 5/1999 | Sholder et al. ............... 607/27 |
| 5,899,931 A | 5/1999 | Deschamp et al. ........... 607/60 |
| 5,907,291 A | 5/1999 | Chen et al. |
| 5,913,827 A | 6/1999 | Gorman .................... 600/509 |
| 5,917,414 A | 6/1999 | Oppelt et al. ........... 340/573.1 |
| 5,919,141 A | 7/1999 | Money et al. .............. 600/513 |
| 5,919,214 A | 7/1999 | Ciciarelli et al. ............. 607/32 |
| 5,929,782 A | 7/1999 | Stark et al. |
| 5,931,791 A | 8/1999 | Saltzstein et al. ........... 600/513 |
| 5,935,078 A | 8/1999 | Feierbach .................. 600/509 |
| 5,944,659 A | 8/1999 | Flach et al. ................. 600/300 |
| 5,949,352 A | 9/1999 | Ferrari .................... 340/870 |
| 5,954,536 A | 9/1999 | Fuerst et al. ............... 439/493 |
| 5,954,539 A | 9/1999 | Hornung ................... 439/590 |
| 5,954,719 A | 9/1999 | Chen et al. ................... 606/42 |
| 5,957,854 A | 9/1999 | Besson |
| 5,959,529 A | 9/1999 | Kail, IV ..................... 340/539 |
| 5,960,119 A | 9/1999 | Echigo et al. .............. 382/248 |
| 5,961,448 A | 10/1999 | Swenson et al. ............ 600/301 |
| 5,963,650 A | 10/1999 | Simionescu et al. .......... 380/49 |
| 5,964,701 A | 10/1999 | Asada et al. ................ 600/300 |
| 5,966,692 A | 10/1999 | Langer et al. ................. 705/3 |
| 5,970,105 A | 10/1999 | Dacus ........................ 375/344 |
| 5,995,861 A | 11/1999 | Price .......................... 600/372 |
| 5,999,857 A | 12/1999 | Weijand et al. ............... 607/60 |
| 6,006,125 A | 12/1999 | Kelly et al. ................. 600/382 |
| 6,009,350 A | 12/1999 | Renken ....................... 607/32 |
| 6,010,359 A | 1/2000 | Etters et al. ................ 439/496 |
| 6,027,363 A | 2/2000 | Watt et al. .................. 439/456 |
| 6,039,600 A | 3/2000 | Etters et al. ................ 439/496 |
| 6,047,201 A | 4/2000 | Jackson, III ................ 600/344 |
| 6,053,887 A | 4/2000 | Levitas et al. ................. 604/49 |
| 6,057,758 A | 5/2000 | Dempsey et al. ........... 340/539 |
| 6,066,093 A | 5/2000 | Kelly et al. ................. 600/386 |
| 6,073,046 A | 6/2000 | Patel et al. ................. 600/509 |
| 6,074,345 A | 6/2000 | van Oostrom et al. ...... 600/300 |
| 6,076,003 A | 6/2000 | Rogel ........................ 600/390 |
| 6,077,124 A | 6/2000 | Etters et al. ................ 439/632 |
| 6,083,248 A | 7/2000 | Thompson ................... 607/30 |
| 6,086,412 A | 7/2000 | Watt et al. .................. 439/496 |
| 6,093,146 A | 7/2000 | Filangeri .................... 600/300 |
| 6,102,856 A | 8/2000 | Groff .......................... 600/301 |
| 6,117,076 A | 9/2000 | Cassidy ...................... 300/300 |
| 6,141,575 A | 10/2000 | Price .......................... 600/372 |
| 6,146,190 A | 11/2000 | Fuerst et al. ............... 439/496 |
| 6,147,618 A | 11/2000 | Halleck et al. ............. 340/669 |
| 6,149,602 A | 11/2000 | Arcelus ...................... 600/523 |
| 6,154,676 A | 11/2000 | Levine ......................... 607/58 |
| 6,163,276 A | 12/2000 | Irving et al. |
| 6,184,797 B1 | 2/2001 | Stark |
| 6,198,394 B1 | 3/2001 | Jacobsen et al. ......... 340/573.1 |
| 6,206,837 B1 | 3/2001 | Brugnoli ..................... 600/529 |
| 6,208,889 B1 | 3/2001 | Gorman ..................... 600/520 |
| 6,213,942 B1 | 4/2001 | Flach et al. ................. 600/300 |
| 6,225,901 B1 | 5/2001 | Kail, IV ..................... 340/539 |
| 6,236,874 B1 | 5/2001 | Devlin et al. .............. 600/372 |
| 6,238,338 B1 | 5/2001 | DeLuca et al. ............. 600/300 |
| 6,244,890 B1 | 6/2001 | Fuerst et al. ............... 439/357 |
| 6,252,883 B1 | 6/2001 | Schweickart |
| 6,267,723 B1 | 7/2001 | Matsumura et al. ........ 600/300 |
| 6,287,252 B1 | 9/2001 | Lugo .......................... 600/300 |
| 6,289,238 B1 | 9/2001 | Besson et al. .............. 600/509 |
| 6,295,466 B1 | 9/2001 | Ishikawa et al. ............ 600/509 |
| 6,304,774 B1 | 10/2001 | Gorman ..................... 600/520 |
| 6,319,200 B1 | 11/2001 | Lai et al. .................... 600/300 |
| 6,332,094 B1 | 12/2001 | Gorman ..................... 600/520 |
| 6,364,834 B1 | 4/2002 | Reuss et al. ................ 600/300 |
| 6,389,308 B1 | 5/2002 | Shusterman ................ 600/509 |
| 6,416,471 B1 | 7/2002 | Kumar et al. .............. 600/300 |
| 6,440,067 B1 | 8/2002 | DeLuca et al. ............. 600/300 |
| 6,441,747 B1 * | 8/2002 | Khair et al. ........... 340/870.16 |
| 6,450,953 B1 | 9/2002 | Place et al. ................. 600/300 |
| 6,480,733 B1 | 11/2002 | Turcott ....................... 600/516 |
| 6,496,705 B1 | 12/2002 | Ng et al. .................... 455/502 |
| 2002/0038094 A1 | 3/2002 | Gorman ..................... 600/520 |

* cited by examiner

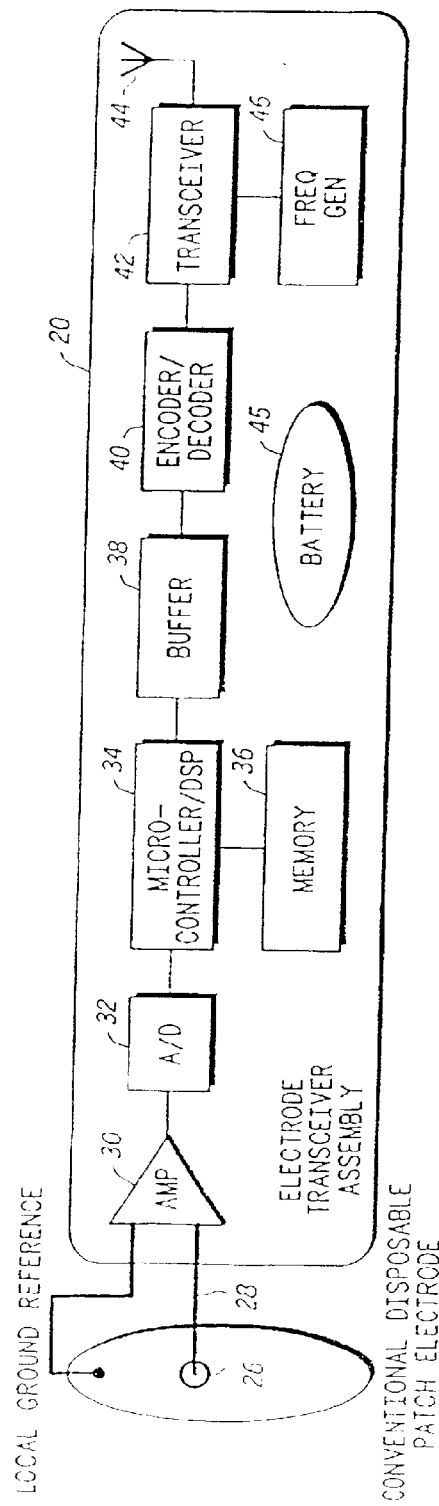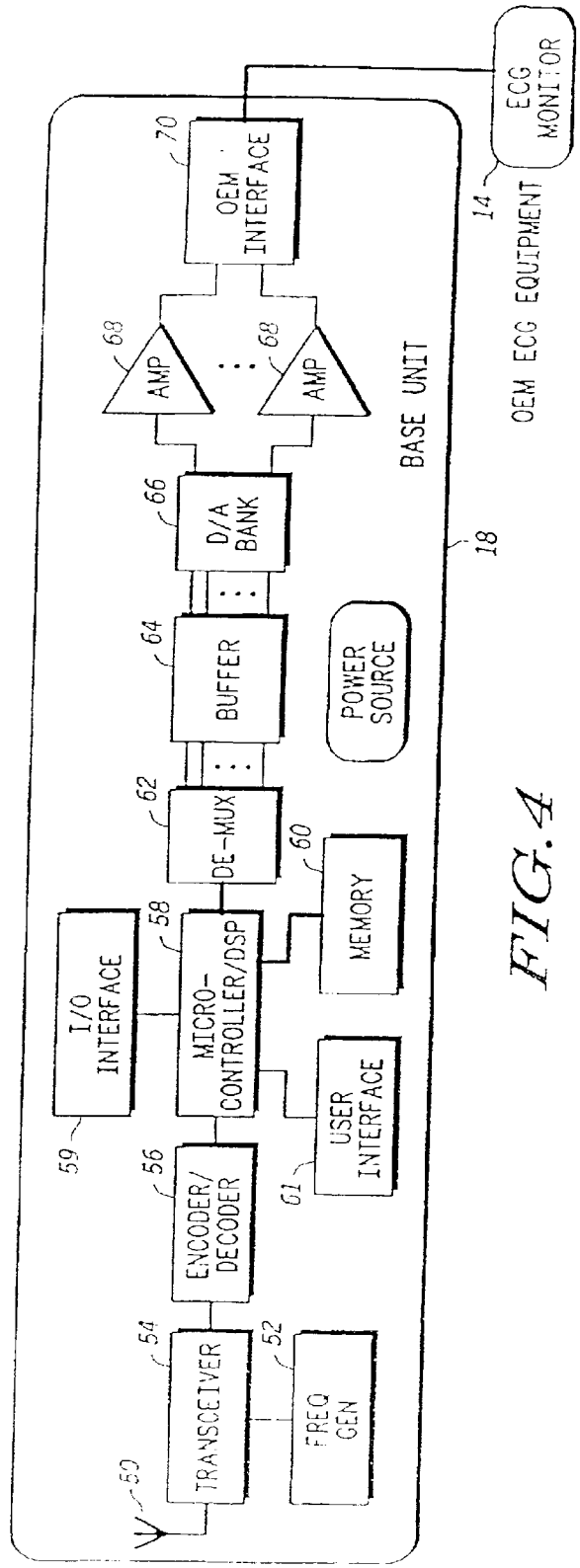

DAC CONFIGURATION

AMPLIFIER GAIN CONFIG

FILTER BAND SELECTION

CARRIER SIGNAL SELECTION

ACQUISITION START

ACQUISITION STOP

ERROR DATA RETRANSMIT

DAC AUDIT

REGISTRATION SCENARIO (ON A DEDICATED CHANNEL)

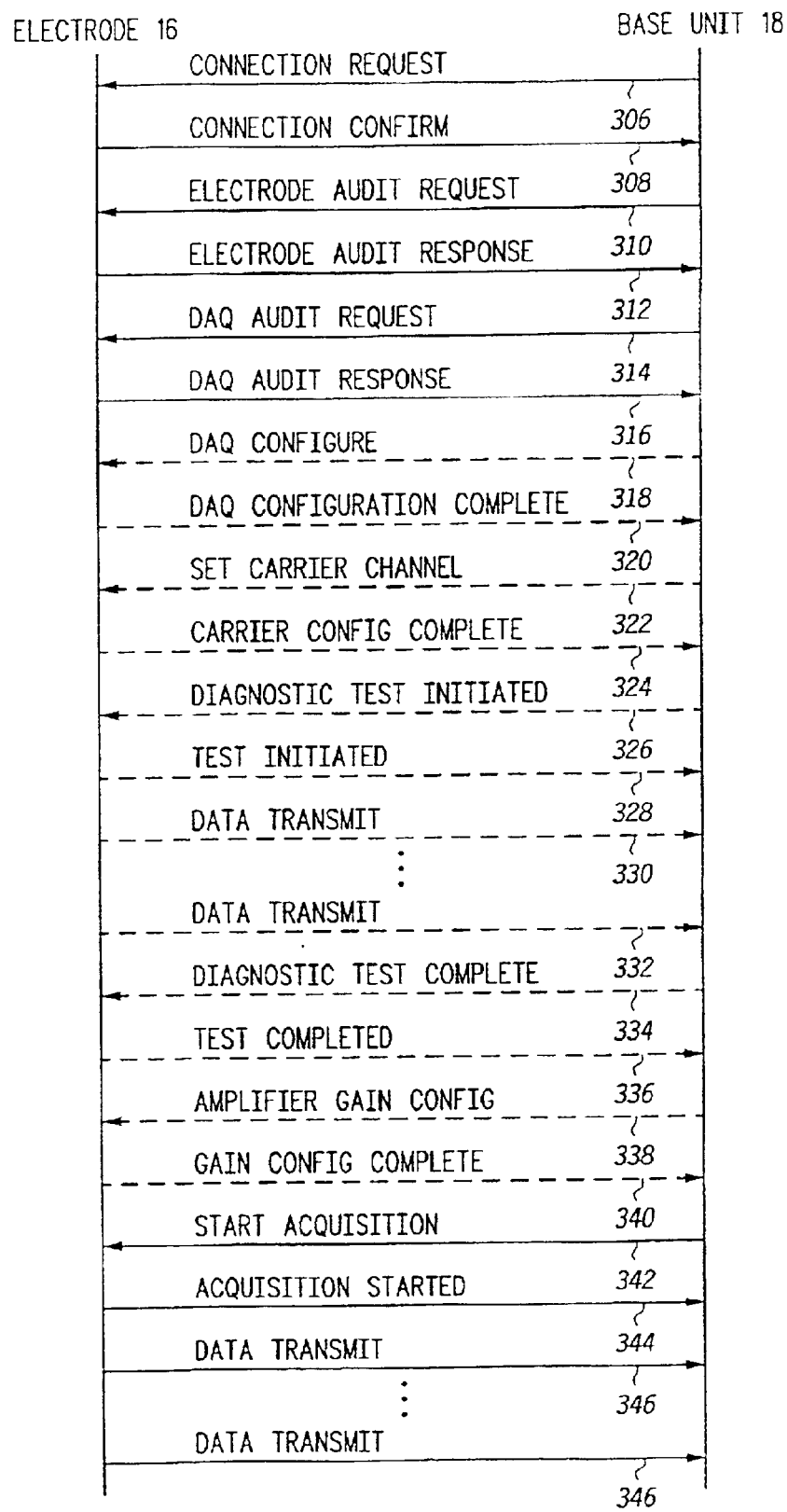
FIG.28  SIGNAL LOSS/CHANNEL ERROR RECOVERY SCENARIO

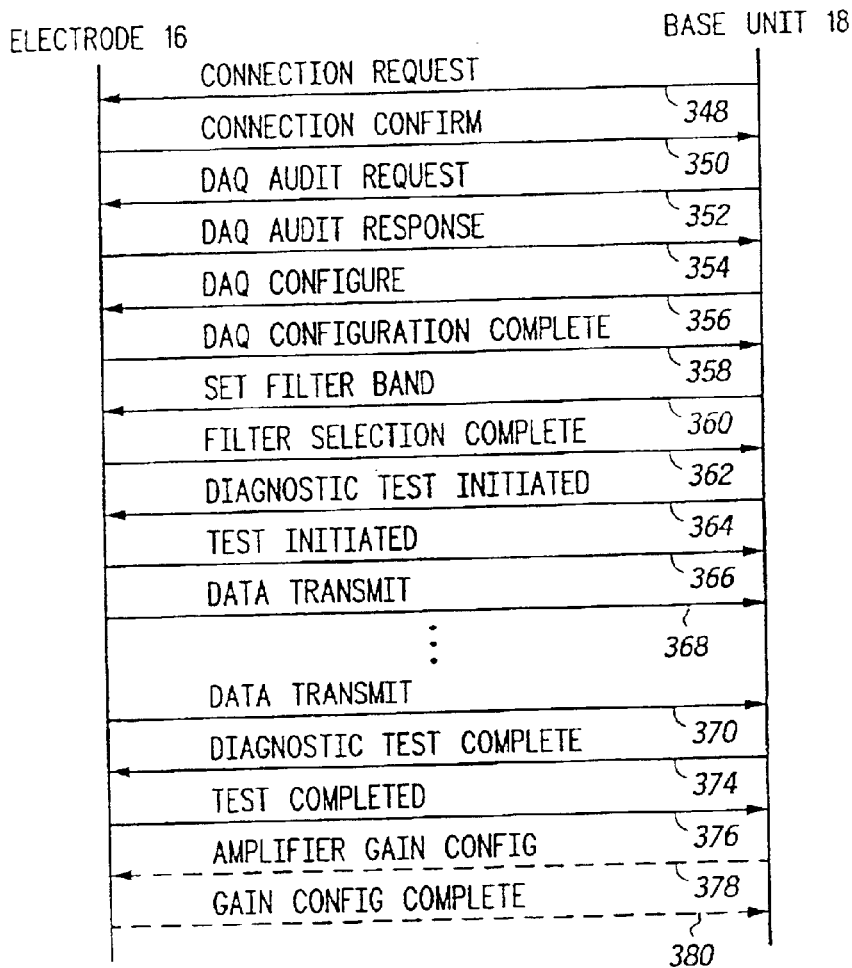
FIG. 29  MONITORING CONFIGURE SCENARIO
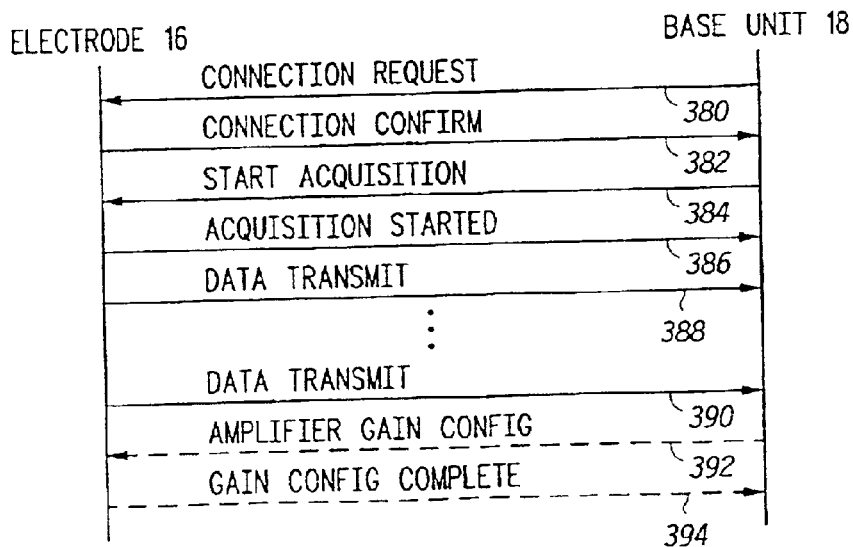
FIG. 30  MONITORING START SCENARIO

WIRELESS E-TRADE LOGIC DIAGRAM

BASE UNIT LOGIC DIAGRAM

SENSOR INITIALIZATION
WITH RESET CONNECTION

SENSOR ACTIVATION

SENSOR DATA ACQ CONTROL

WIRELESS SYSTEM PROTOCOL FOR TELEMETRY MONITORING

"This application is a division of application Ser. No. 09/551,719, filed Apr. 18, 2000, now U.S. Pat. No. 6,441,747 which is hereby incorporated by reference herein."

BACKGROUND OF THE INVENTION

A. Field of the Invention

This invention relates generally to the field of devices used to measure electrical biopotential signals generated by a human body, such as electrocardiogram (ECG), electroencephalogram (EEG) and electromyography (EMG) signals. More particularly, the invention relates to a wireless signal acquisition system and over the air communications protocol that is used between a plurality of wireless, remotely programmable transceivers, each coupled to a conventional patch electrode, and an associated base unit. The base unit obtains a patient's ECG, EEG or EMG signal from the wireless transceivers and supplies the signal to monitor unit for display. The wireless communications protocol allows the base unit to remotely configure and manage the wireless transceivers, prior to and during data acquisition and transmission.

B. Statement of Related Art

Conventional ECG monitoring typically requires direct wired electrical connections between electrodes that are attached to the body of the patient at one end and to an ECG monitor on the other end. Electric bio-potentials are measured at the electrodes and signals are transformed via bipolar and unipolar leads into an electrocardiogram.

Conventional ECG apparatus for hospital bedside monitoring typically requires up to ten wired electrodes. Each electrode is attached to the body of the patient, and has a wire, several feet or more in length, leading to an ECG monitor. The lengthy wired electrodes of conventional ECG apparatus obstruct the patient and limit the patient's freedom of movement. They are also cumbersome for the physician or assisting nurse.

Telemetry systems for wireless ECG monitoring for patients in hospitals currently exist. These systems are more expensive, intended for greater range (higher power), and do not totally eliminate the physical electrode wires attached to the patient. Instead of being connected to the monitor, the electrodes are each wired to a single transmitter box that is worn by the patient. Some telemetry systems also may not handle a 12 lead ECG (10 wires) because of the wiring that is required between the electrodes and the transmitter box. For example, the Spacelabs Ultraview Modular Digital Telemetry system can only handle a maximum of four leads (5 wires).

Wireless medical monitoring and diagnosis systems have been proposed in the prior art. U.S. Pat. No. 5,862,803 to Besson et al. describes a wireless electrode/sensor patch system with sensor, controller and transceiver electronics contained in an electrode patch assembly. U.S. Pat. Nos. 5,307,818, 5,168,814 and 4,981,141, all issued to Segalowitz, describe a wireless electrode system for ECG monitoring. The Besson et al. and Segalowitz patents are incorporated by reference herein. The Segalowitz patents describe a single piece electrode patch with built-in microchips for wireless one way communication, and a snap on electronic-assembly that fastens to a disposable electrode patch. However, the electrode patch is a special two-conductor type that is not conventional. The electrode assemblies are either transmit only or receive only (not both). A reference signal (generated from a Wilson network) is transmitted from the base unit to only the Right Leg electrode patch, which is receive only. Electrodes can only be programmed via manual switches on the electrode casing, not over-the-air from the base unit. For the multiple electrode embodiment, the base unit contains multiple receivers and antennas which imply multiple transmit frequencies are required for the system and over-the-air signaling (thus making the base unit more costly to implement). There is no mention of error correction or detection capability in the electrodes or base unit.

In another embodiment of the Segalowitz '818 patent, there is discussion of a single strip assembly which contains all of the electrodes required for 12-lead ECG monitoring with microchip circuitry contained in the strip assembly (not in the individual electrode patches). In this configuration, the ECG signals from each electrode are multiplexed and transmitted from a single transmitter (contained in the strip assembly) via time multiplexing on a single digitally encoded frequency channel. However, no time multiplexing on a single frequency channel is discussed for their multiple transmit electrode embodiment.

The purpose of the invention is to define a communication protocol, i.e., set of command procedures, for a wireless (leadless) electrode system that replaces the physical wires between the electrodes attached to the patent and the monitoring system base unit. The definition of communication protocols or procedures for programming the electrodes over-the air is necessary to provide flexibility in configuring the wireless electrode system to the variable environmental conditions that exist across a wide scope of patent population, as well as different application area or needs. The wireless system allows the patient a greater degree of mobility within the neighboring area without worry about accidentally disconnecting the electrodes or being disconnected from the monitoring equipment. A wireless monitoring system also provides better patient safety since the patient is electrically isolated from the monitor. This monitoring system is also more immune to noise artifacts since the digitization process of the data occurs right at the electrode measurement point and not through extended wires. The protocol defined herein describes initialization, configuration, and management of the wireless electrode network. It also describes data acquisition and transfer to the base unit that synchronizes and coordinates electrode functions.

SUMMARY OF THE INVENTION

An improvement to a wireless system for medical monitoring is provided. The wireless system has a base unit and a plurality of wireless sensors for attachment to a patient's body. In accordance with the invention, each of the wireless sensors has a transceiver assembly for transmitting and receiving two-way wireless communications with a base unit. The transceiver assembly includes a computing platform (such as a microcontroller) and a memory storing a set of instructions for execution by the computing platform in response to commands received from the base unit.

The base unit is provided with a wireless transceiver for transmitting and receiving wireless communications with the sensors. The wireless communications include, among other things, commands for the transceiver assemblies. Further, a set of instructions is provided in the base unit, such as in a memory for a base unit microcontroller, wherein the base unit issues the commands to the transceiver assemblies in response to the execution of the instructions. The commands from the base unit and the responses to those commands from the transceiver assemblies comprise a procedure or protocol by which the base unit may remotely, and automatically, manage and configure the transceiver assemblies during real time as the transceiver assemblies acquire and transmit physiologic signal data to the base unit.

The wireless communications procedures described herein are particularly well suited for use in a system acquiring EEG, ECG or EMG signals from a human patient. The programmable wireless transceivers are associated with a sensor in the form of a conventional patch electrode, and acquire bio-potential signals between conductors in the electrode. The patch electrodes are of conventional design and adapted to be placed on the surface of the patient's body for measuring electrical bio-potentials.

A robust wireless monitoring system needs to allow ease of configuration and calibration due to the variability of physiology across patient populations. The present invention describes wireless programming procedures that allow flexibility in configuration of telemetry based electrode system to adapt to changing requirements of different applications. This invention provides for procedures that are not only specific to ECG, but can equivalently be applied in other application areas such as EEG, EMG, EOG, Respiratory, Tonometric Blood Pressure, Temperature and other wireless medical monitoring systems. Furthermore, the programming procedures are dynamic, responsive to real time conditions as data is being acquired and transmitted to the base unit.

The protocol provides for transmission of a variety of configuration commands. Examples of such commands include registration information, data acquisition control commands (such as start and stop messages), transmission frequency commands, time slot commands, amplifier gain commands, transmitter control commands, power saving mode commands, initialization commands, and so forth.

The ability to remotely program the wireless transceivers gives considerable flexibility over how the electrodes are configured and positioned on the patient's body. The programmable wireless transceivers could be designed to be installed on particular locations of the patient's body, such as left arm, right arm, left leg, etc. In a more preferred embodiment, the remotely programmable electrode transceivers are generic with respect to particular placement locations on the surface of a patient's body. The base unit transmits programming data to the individual wireless transceivers. The programming data includes electrode position location data associated with a unique placement position to be assigned to the individual wireless transceivers, as well as electrode identification data. When the data is acquired from each of the wireless transceivers, the electrode identification data, electrode position location data and the acquired electrode signal are sent from the wireless transceivers to the base unit.

The base unit and the wireless transceivers may use time division multiplexing as a communications format for transfer of the acquired signals to the base unit. In this case, the base unit transmits a global time base signal to the plurality of individual wireless transceivers. The global time base signal is used for synchronizing the timing of transmission of signals acquired by the individual wireless transceivers to the base unit in discrete time slots in a single frequency channel. This time division multiplexing provides that each wireless transceiver transmits its signals to the base unit in discrete time slots, with the wireless transceivers sharing a common frequency channel.

These and still other aspects and features of the invention will be more apparent from the following detailed description of a presently preferred embodiment. In this specification, the terms "wireless transceiver" and "programmable wireless transceiver" are meant to refer to the wireless electrode transceiver assembly as a unit, as distinguished from the actual transceiver module within the assembly, unless the context clearly indicates otherwise. Further, the use of the term "electrode" is meant to be interpreted broadly to cover bio-sensors generally.

BRIEF DESCRIPTION OF THE DRAWINGS

A presently preferred embodiment of the invention is described below in conjunction with the appended drawing figures, wherein like reference numerals refer to like elements in the various views, and in which:

FIG. 3 is a block diagram of the wireless transceiver assembly of FIG. 2;

FIG. 4 is a block diagram of the base unit of FIG. 1;

FIG. 28 is an illustration of a signal loss and error recovery procedure implemented by the base unit in the event of a loss of signal from one of the electrode assemblies of FIG. 1;

FIG. 29 is an illustration of a monitoring configuration procedure;

FIG. 30 is an illustration of a monitoring start procedure;

DETAILED DESCRIPTION OF THE PREFERRED EMBODIMENT

The present invention can be used in a system consisting of multiple smart wireless transceiver devices sized to snap onto conventional disposable patch wireless sensors or electrodes for wireless patient monitoring, and a base unit communicating with the wireless transceivers that is also capable of interfacing to existing conventional bedside monitoring equipment, such as a standard ECG or EEG monitor. The wireless transceivers receive commands from the base unit such as registration information, transmission frequency commands, amplifier gain commands, transmitter control commands, power saving mode, etc. and include hardware and software or firmware for processing these commands and responsively configuring the wireless transceiver accordingly. These commands are the result of execution of program instructions in a computing platform, such as a microcontroller, in the base unit and a set of response instructions in a computing platform in the wireless transceivers.

A global time base signal is transmitted from the base unit to the electrodes to serve in synchronizing the timing of acquisition of sample points for all electrodes used in measuring input body surface potentials (e.g., ECG signal). In the ECG example, the base unit receives the transmitted ECG signal from each electrode (at predetermined time intervals if time division multiplexing is the embodiment of the communication protocol), demodulates, decodes (with error correction), digitally processes the data, applies any needed signal conditioning (amplification, filtering), and converts back to analog form for outputting the ECG signals to the standard ECG equipment for display. The base unit also has a universal interface to existing standard ECG equipment so that the wireless link between the electrodes and base unit appears transparent to the ECG equipment. The ECG equipment will accept the individual electrode signals for developing any required lead configuration.

The wireless transceivers and base unit use a unique over-the-air communication protocol between the base unit and the electrodes which allows wireless programming (configuration), identification, auditing, data acquisition control, and transmitter control of each electrode used in the system during real time. For frequency bandwidth efficiency of the invention, the system could be designed such that transmission of multi-channel signals is on a single digitally encoded frequency channel between the base unit transceiver and multiple electrode devices by using time division multiplexing. For example, each electrode will receive synchronization data from the base unit on the same receive frequency, and instruction on which time slot to transmit it's digitally encoded data. This makes it possible for multiple patients each on a separate frequency channel to use the wireless system in the same hospital room if there is limited bandwidth.

Figure 1:
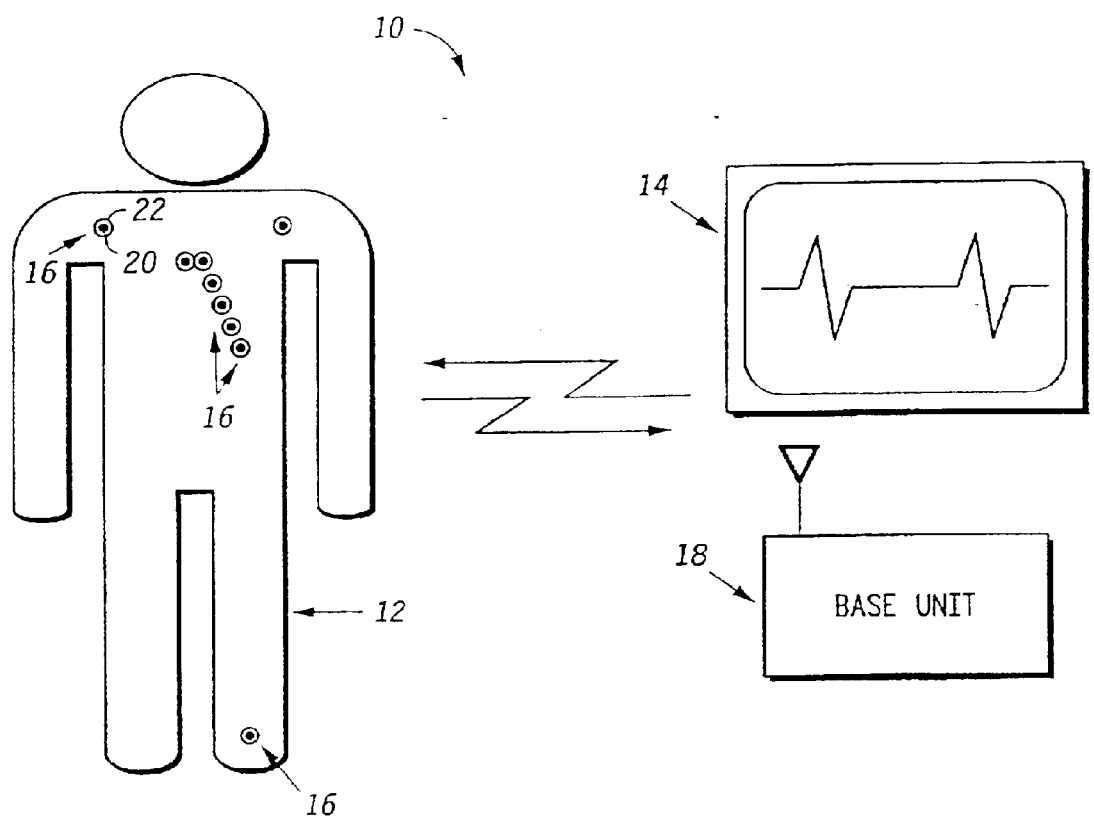
FIG. 1 is a schematic representation of the system of the present invention in use with a patient to acquire ECG signals from the patient and supply them to a ECG monitor.

Referring now to FIG. 1, a system 10 according to a presently preferred embodiment is shown schematically for use with a patient 12. The system 10 acquires ECG, EMG, EEG or other types of signals from the patient 12 and supplies them to a monitor 14. The present example will be discussed in terms of an ECG system, but the invention is directly applicable to other types of medical monitoring.

The system 10 is a wireless system, in that a plurality of electrode assemblies 16 receive commands (e.g., synchronization and control commands) from a base unit 18 using wireless transmission methods, and supply the ECG signals to the base unit 18 using wireless transmission methods as well. Thus, cumbersome wires for the electrode assemblies 16 are eliminated in the illustrated embodiment.

The electrode assemblies 16 of FIG. 1 consist of a plurality of individual, remotely programmable wireless transceiver assemblies 20, each transceiver assembly designed to snap onto a conventional patch electrode 22 (such as the 3M Red dot electrode) used in ECG monitoring. The wireless transceivers 20 are described in further detail in conjunction with FIGS. 2 and 3. The base unit 18 includes a wireless transceiver for sending and receiving messages to the plurality of individual wireless transceivers, and is described in further detail in conjunction with FIGS. 4, 6, 8 and 9. The base unit further has an interface for providing analog ECG signals received from the wireless transceivers 20 to a conventional ECG display monitor 14.

Figure 5:
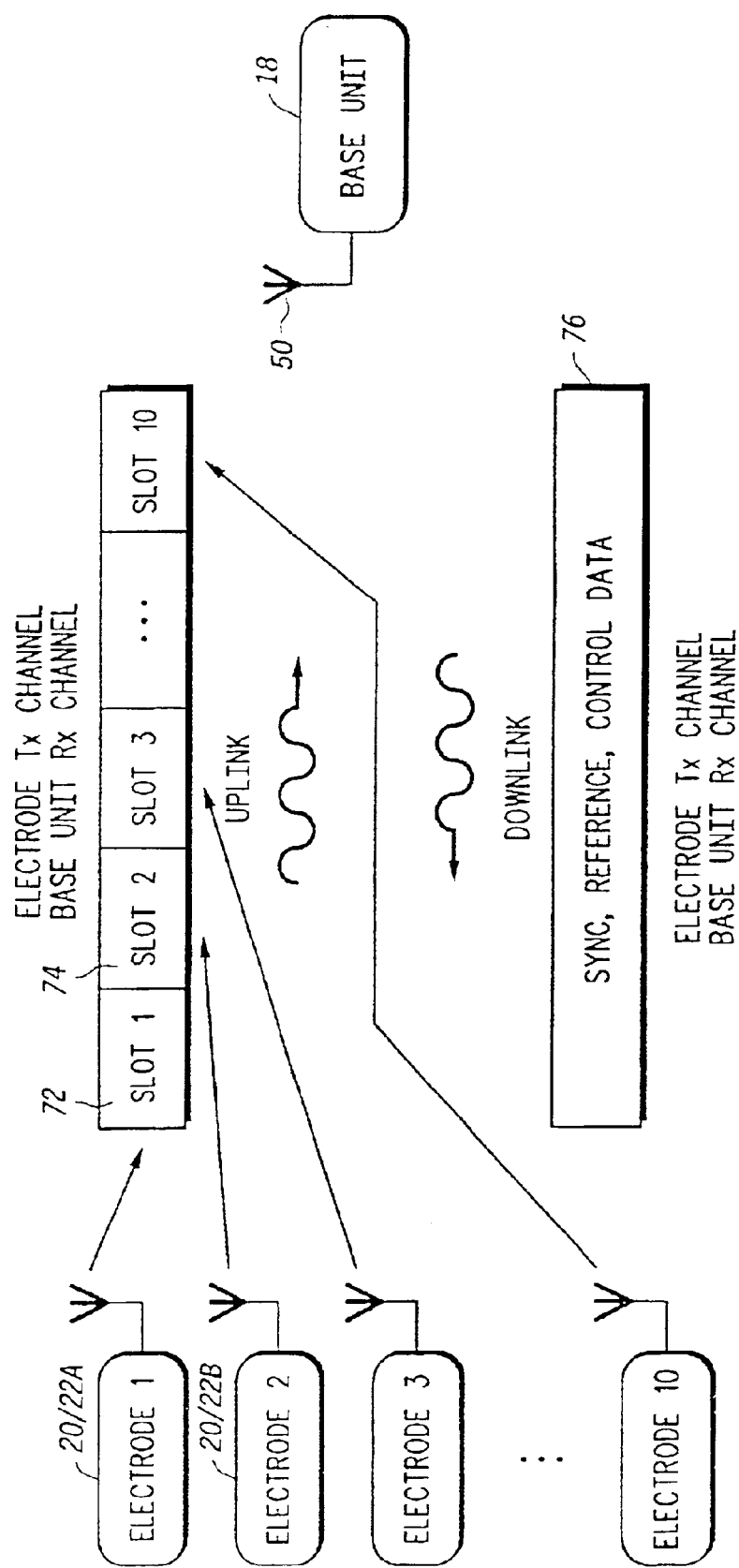
FIG. 5 is a diagram illustrating the time division multiplexing of transmission format for the plurality of wireless transceivers of FIG. 1 in the uplink direction (the direction of wireless transmission from the wireless transceivers to the base unit), and the transmission of synchronization, reference and control data from the base unit to the wireless transceivers in a common channel in the downlink direction.

A preferred communications format for wireless communication between the base unit 18 and the wireless transceivers 20 is time division multiplexing in a common frequency channel in the uplink direction, that is between the transceivers and the base unit. Each wireless transceiver 20 transmits ECG signals in a particular time slot in the channel, as indicated in FIG. 5. In the downlink direction, the base unit transmits control commands and other information in a common channel that all the wireless transceivers are tuned to. The time slot assignment, frequency assignment, and other transmission control information is managed and controlled by the base unit 18, as described in further detail below. An alternative embodiment is to use code division multiple access (CDMA) communication format for wireless communication between the base unit 18 and the wireless transceivers 20.

The messages transmitted by the base unit 18 also include configuration commands for the wireless transceivers 20. These configuration commands can be, for example, change or set the data acquisition sampling rate, amplifier gain setting, and channel carrier settings, and can also consist of a timing signal for synchronization of the transmission time slot. Preferably, the base unit 18 transmits a global time base signal to all of the wireless transceivers. The global time base signal synchronizes the timing of transmission of the ECG signals acquired by all of the wireless transceivers 20, such that the transmissions are in discrete time slots in a single frequency channel, as shown in FIG. 5.

The details of the over-the-air programming protocol to exchange messages and information between the base unit and the transceivers may be arrived at in many ways within the spirit of the present invention, and is considered within the ability of a person skilled in the pertinent art from the present disclosure. In one possible embodiment, packets of data are transmitted between the base unit and the wireless transceivers. Particular fields in the packets (bytes of data) are reserved for control data, payload data, CRC or error correction data, etc. in accordance with known wireless transmission protocols, conventional data transmission techniques such as IP or Ethernet, or similar techniques. A presently preferred protocol and message structure is described later in this document in conjunction with FIGS. 11–30.

Figure 2:
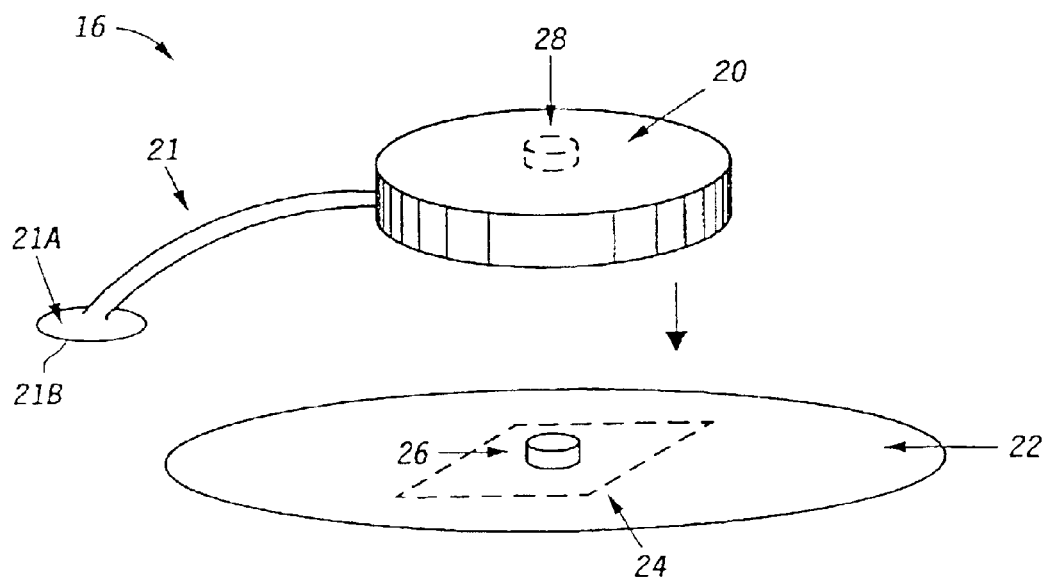
FIG. 2 is a detailed perspective view of one of the patch electrodes and associated remotely programmable wireless transceiver of FIG. 1, it being understood that all of such patch electrodes and wireless transceivers of FIG. 1 are of a construction similar to that shown in FIG. 2.

FIG. 2 is a detailed perspective view of one of the patch electrodes 22 or sensors and associated remotely programmable wireless transceiver 20 assembly 16 of FIG. 1, it being understood that all of such patch electrodes and wireless transceivers of FIG. 1 are of a construction similar to that shown in FIG. 2. The patch electrode 22 is adhered to the surface of the patient's body 12 in conventional fashion. The patch electrode 22 includes a conductor 24 supplying ECG or other signals to a pin 26. The pin 26 is received in complementary pin receiving structure 28 in the wireless transceiver 20 so as engage (as in a snap fit) the two parts 20 and 22.

The pin receiving structure 28 conducts electrical impulses with respect to a local ground reference to electronic circuitry in the wireless transceiver 20. The local ground reference consists of a flexible strip 21 connected to the transceiver 20 having a tip or skin contact 21A, made from a conductive material, which is placed underneath the patch electrode 22 in contact with the skin. The purpose is to allow the transceiver to measure the bio-potential difference between the signal contact point 26 and the local ground reference 21/21A. The material used for the strip 21 could be a thin flexible material such as plastic with an internal conductive trace or lead wire from the transceiver 20 to the skin contact point 21A. The skin contact point 21A is preferably coated with conductive silver chloride (AgCl) material 21B on one side thereof.

FIG. 3 is a block diagram of the wireless transceiver of FIGS. 1 and 2. The transceiver assembly 20 snaps onto the post pin 26 of a disposable conventional patch electrode. Electrical signals provided from the electrode 22 are supplied to a low noise, variable gain amplifier 30 in the wireless transceiver 20. The amplifier 30 may include a pre-amp stage. The analog signal is filtered, sampled and converted to digital signals in the A/D converter 32. The digital signals are supplied to a computing platform, illustrated as a microcontroller/Digital Signal Processor 34. The microcontroller performs signal processing of the digital signal supplied by the A/D converter 32. The signal processing functions include noise filtering and gain control of the digital ECG signal. In an alternative but less-preferred embodiment, gain control in the transceiver assembly could be performed by adjustment of the amplifier 30 gain in the analog signal path. The microcontroller also processes commands and messages received from the base unit, and executes firmware instructions stored in a memory 36. The memory further stores a unique electrode identifier as described in further detail below. The memory may also store a position location identifier or data associated with a position the electrode is attached to the patient. The position location identifier or data is dynamically programmable from the base unit.

The processed digital ECG signals are buffered in a buffer 38, supplied to an encoder/decoder 40 and fed to a RF transceiver module 42 for transmission to the base unit via a low power built-in RF antenna 44. The transceiver 42 includes a modulator/demodulator, transmitter, power amp, receiver, filters and an antenna switch. A frequency generator 46 generates a carrier frequency for the RF transmission. The frequency is adjustable by the microcontroller 34. A battery 45 with a negative terminal connected to a local ground reference provides DC power to the components. The microcontroller/DSP 34 controls the frequency generator 46 so as to select a frequency for wireless transmission of data and control messages to the base unit. The microcontroller in the computing platform 34 also executes an initialization routine wherein the receiver scans a default receive channel for commands from the base unit, and if the commands are received the transmitter transmits identification information in an assigned frequency and time slot to the base unit.

All or some of the individual blocks shown in FIG. 3 could be combined in a microchip or microchips to miniaturize the size of the snap-on wireless transceiver assembly 20.

Referring now to FIG. 4, the base unit 18 is shown also in block diagram form. The base unit 18 transmits commands to all of the wireless transceivers and instructs each transceiver to transmit its ECG data individually (such as in time division multiplexing). The base unit receives the transmitted ECG signals from the electrodes (up to 10) in sequence and then demodulates, decodes, error corrects, de-multiplexes, buffers, signal conditions, and reconverts each electrode's data back to an analog signal for interfacing to the standard ECG monitor 14. The base unit also transmits programming information to the electrodes for frequency selection, power control, etc.

The base unit 18 includes a low power RF antenna 50, a frequency generator 52 for generating a carrier frequency and an RF transceiver 54. The transceiver 54 includes a modulator/demodulator, transmitter, power amp, receiver, filters and an antenna switch. The base unit further includes a encoder/decoder 56, a computing platform such as a microcontroller/Digital Signal Processor (DSP) 58, and a memory 60 storing code for execution by the microcontroller/DSP, and I/O interface 59 for connection to a personal computer which is used as a test port for running system diagnostics, base unit software upgrades, etc., and a user interface 61. The user interface 61 may consist of the following: a display for indicating electrode programming information or error/alarm conditions, a keypad or buttons for user requested inputs, an alarm unit for audibly indicating error/alarm conditions (for example a detached, low battery or failed electrode), and LEDs for visually indicating error, alarm or programming status.

The time slot ECG data received from the wireless transceivers is demultiplexed in demultiplexer 62 and supplied to a buffer 64. A digital to analog filter bank 66 converts the multiple channels of digital data from the wireless transceivers to analog form. The analog signals are amplified by amplifiers 68 and supplied to an OEM (original equipment manufacturer) standard ECG monitor interface 70. The interface 70 could be either part of the base unit 18 assembly so that it can directly plug into the ECG display equipment 14 via a standard connector, or it could be part of a cable connection to the display equipment. The idea with the OEM interface 70 is to supply multiple analog ECG signals to the conventional ECG display equipment already used in the hospital environment, in a compatible and transparent manner, such that the display equipment would treat the signals as if they were generated from conventional wired electrodes. Familiarity with the analog signal acquisition hardware or electronics for the ECG display equipment 14 will be required obviously, and the OEM interface circuitry may vary depending on the manufacturer of the display equipment. The OEM monitor interface detailed design is considered within the ability of a person skilled in the art.

Referring to FIG. 5, a possible transmission scheme between the wireless transceivers 20 and the base unit 18 is time division multiplexing. This allows a single transmit frequency to be used by all the electrodes in the ECG system. All electrodes receive commands and synchronization data (time base signal, reference signal and control data 76) from the base unit 18 on an assigned receive frequency (downlink) channel. The electrode receive channel may or may not be slotted (time multiplexed). Electrode 1 20/22A transmits it's data on time slot 1 72 (Electrode 2 20/22B on time slot 2 74, etc.) at the assigned transmit frequency (uplink) channel. The base unit 18 receives the transmission from the electrodes 20/22 and demultiplexes, buffers, and reconstructs the individual electrode data.

The system 10 of FIG. 1 utilizes an over the air programming mechanism to exchange messaging and information between the base unit 18 and the wireless transceivers 20. Various types of information could be exchanged. For example, the base unit 18 transmits a data acquisition control message to the wireless transceivers, which tells the microcontroller in the wireless transceivers to start and stop data acquisition. Another command would be a frequency selection command message(s) sent to the wireless transceivers, in which the wireless transceivers responsively select a common frequency channel for transmission of acquired ECG signals to the base unit in discrete time slots.

The following is a list of some of the possible programming commands and messages that could be sent between the base unit and the wireless transceivers:

a. Registration of electrodes 20/22 with the base unit 18. This would include the detection of the electrode type and an associated unique electrode identifier by the base unit. This could also include transmission of a unique base unit identifier to the electrodes (for example where multiple base units are within RF range of the electrodes) and detection of the base unit identifier by the electrode. Also, a patient reference number could also be stored in each electrode so it only receives commands from a specific patient-assigned base unit. Each electrode reference number is also stored in the base unit, so that data coming only from these electrodes is accepted. An additional registration feature would be assignment of a specific electrode function (i.e., position on the patient's body). This is discussed in more detail below. With each of the above commands and messages, the receiving unit would typically transmit back a response message indicating the receipt of the command and sending back any required information to the transmitting unit.
b. Configuration of data acquisition sampling rate.
c. Configuration of amplifier 30 gain setting.
d. Configuration of preamplifier filter band settings.
e. Configuration of carrier channel settings, namely the frequency of the carrier signal generated by the frequency generator 46 in the transceivers.
f. Configuration of timing signal for transmission time slot. This needs to be synchronized with the data acquisition rate.
g. Battery 45 utilization sleep/activation mode.
h. Battery 45 low voltage level detection.
i. Data acquisition start/stop scenario.
j. Data transmit procedure.
k. Error sample data recover/retransmit scenario.
l. System test diagnostic procedure
m. Scan of electrode current channel setting procedure
n. Electrode detection procedure.
o. Electrode status audit.
p. Base unit status audit.
q. Data acquisition subsystem audit.

Electrode Unique Identifier:

The system 10 of FIG. 1 provides a registration mechanism for every wireless transceiver and electrode assembly whereby an electrode identifier is programmed into the base unit, as well as the electrode functional position of the patent (i.e., LA, RA, LL, V1, V2, V3, V4, V5, or V6 in an ECG embodiment). An Electrode Serial Identifier (ESI) will encode the wireless transceiver's unique serial number. Each wireless transceiver is assigned an Electrode Temporary Identifier (ETI) after each registration scenario (on power up or reconfiguration). The temporary identifier can be composed of electrode number and random number for example. The ESI will be included in each message or data transaction from each electrode to the base unit. The electrode identifier will serve to ensure that only registered electrodes input signaling will be accepted by the associated base unit, in the event that two monitoring systems are transmitting on the same frequency channel, or in the case of interference detection.

Base Unit Unique Identifier

The system will provide a registration mechanism whereby a base unit identifier is programmed into the wireless transceiver assemblies being used. The Base Unit Serial Identifier (BUSI) will encode the base unit serial number. During power-up or reconfiguration, a Base Unit Temporary Identifier (BUTI) is assigned and registered with the wireless transceiver assemblies. The base unit identifier will be included in each message or data transaction from the base unit to each wireless transceiver assembly. The base unit identifier will serve to ensure that only the registered base unit input signaling (commands) will be accepted by the assemblies, in the event that two monitoring systems are transmitting on the same frequency channel, or in the case of interference detection.

Electrode System Initialization

Figure 6:
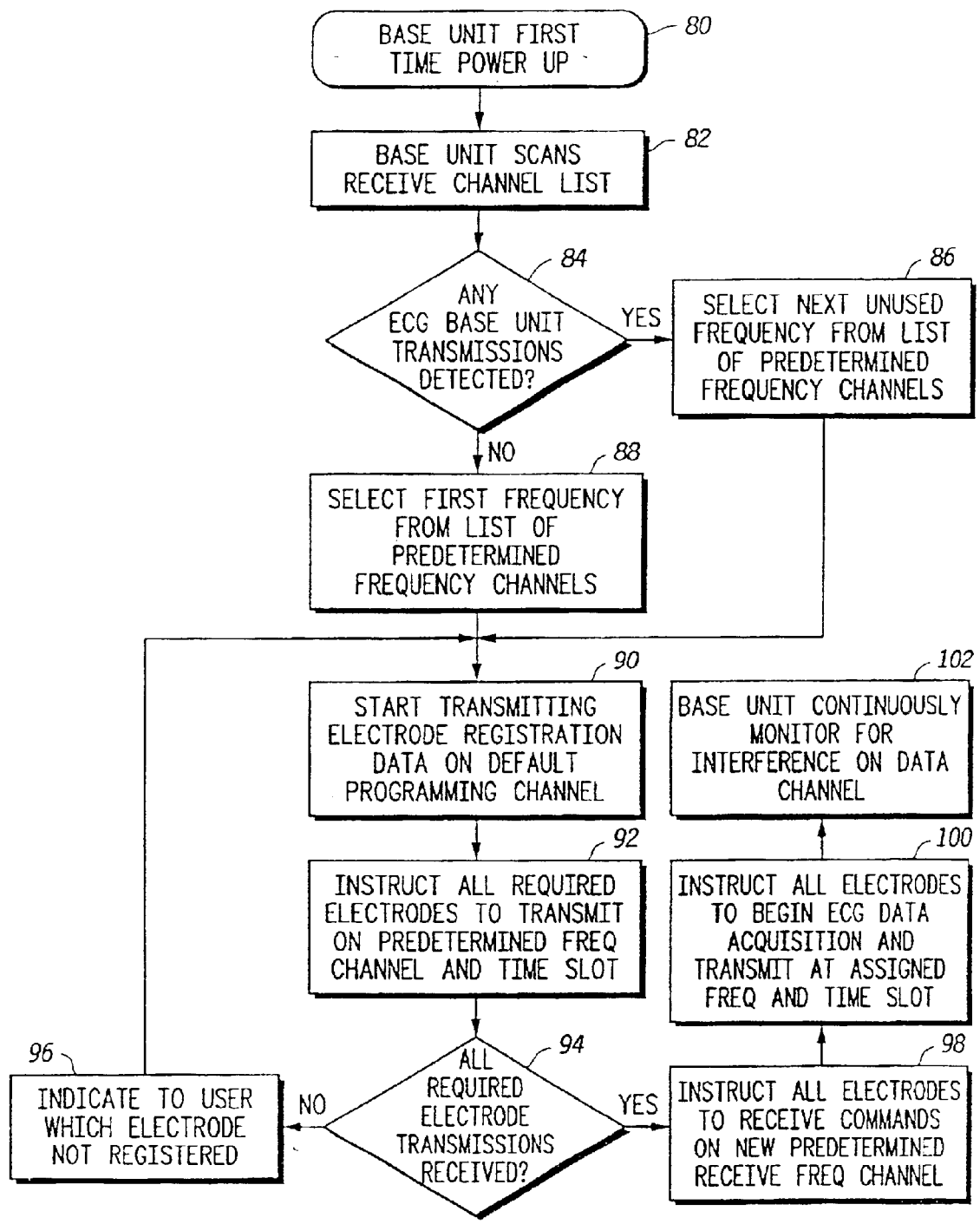
FIG. 6 is a flow diagram illustrating a base unit initialization routine.

FIG. 6 shows a flow diagram of a possible initialization procedure (for both the base unit 18 and electrodes 20/22) for use where the transmission scheme between the base unit and the wireless transceivers 20 is time division multiplexing. This procedure assumes that each electrode in the ECG system contains a unique identifier and a unique functional position ID (i.e., LA, RA, LL, V1, V2, V3, V4, VS, or V6). The procedure of FIG. 6 is reduced to a set of instructions stored in the base unit's memory 60 for execution by the microcontroller 58, as shown in FIG. 4, and in a set of response instructions stored in the wireless transceiver 22's memory and microcontroller of FIG. 3.

Figure 9:
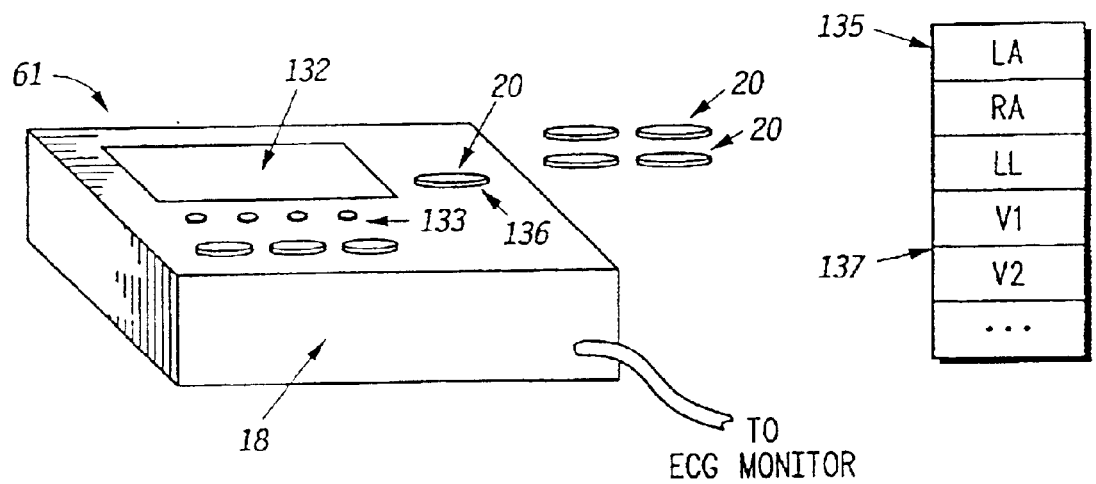
FIG. 9 is a perspective view of a base unit of FIG. 4 and a group of wireless transceivers being initialized according to the procedure of FIG. 8.

At step 80, the base unit is powered up. The base unit is configured for the number of leads used in the ECG system, such as 3, 5 or 12. The configuration could be facilitated by means of any suitable user interface on the base unit 18, such as a display and buttons as shown in FIG. 9 and described subsequently. At step 82, the base unit scans its receive channels, a list of which is programmed into the base unit. At step 84, the base unit determines whether any other ECG base unit transmissions are detected. If so, at step 86 the base unit selects the next unused frequency from the list of predetermined frequency channels as a transmit channel. If not, at step 88 the base unit selects the first frequency from the list of predetermined frequency channels as the transmission channel. The process then proceeds to step 90.

At step 90, the base unit stars transmitting electrode registration data and messages on the default programming channel determined in steps 86 or 88. The registration data and messages include a base unit identification code or serial number. The registration data and messages were described earlier. This insures that the wireless transceivers to be associated with this particular base unit being initialized respond to commands from this base unit and no other base unit. At step 92, the base unit instructs all required electrodes to transmit on a predetermined frequency channel, and assigns time slots to each electrode. The base unit then communicates with electrodes to complete registration. If a particular electrode or electrodes did not complete registration, the base unit indicates via its user interface which electrode is not registered at step 96. If registration is completed for all the electrodes, the base units instruct all electrodes to receive commands on a new predetermined frequency channel at step 98. At step 100, the base unit instructs all electrodes to begin ECG data acquisition and to transmit at the assigned frequency and in the assigned time slot. Step 100 may be started in response to a user prompt via the base unit user interface. During data acquisition, at step 102 the base unit continuously monitors for interference on the receive data channel (uplink direction). If excessive interference occurs (such as from a high bit error rate detected in the base unit microcontroller), the base unit selects a new channel from the list of available frequencies for the electrodes to transmit on and commands a change in transmit frequency.

Figure 7:
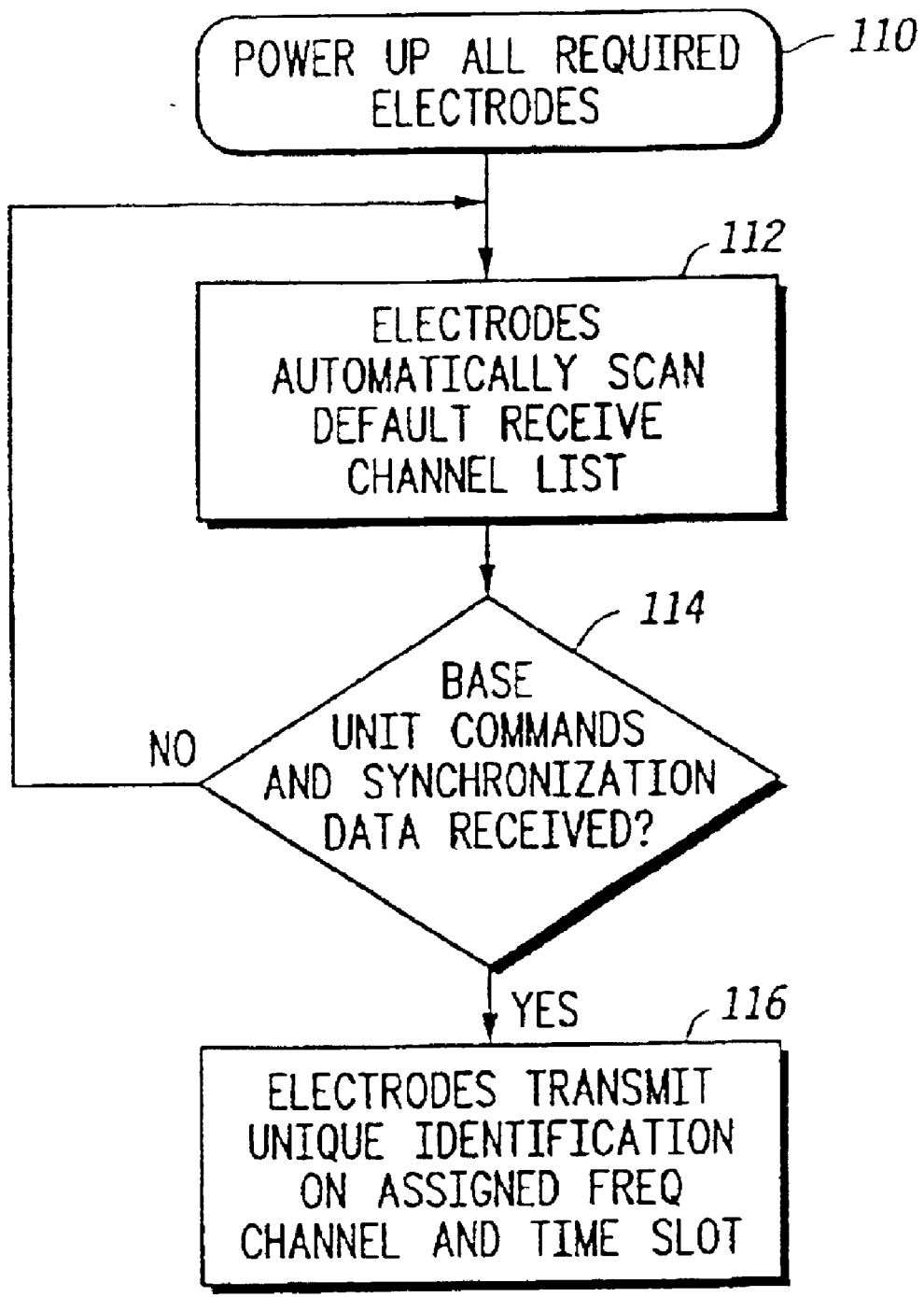
FIG. 7 is a flow diagram illustrating a wireless transceiver initialization routine.

FIG. 7 is a flow diagram of an electrode initialization procedure that may be employed. When the electrodes are initially powered up at step 110, the electrodes will be in a receive only mode. At step 112, the electrodes automatically scan the default receive channel to see if any commands and synchronization signals are being transmitted by the base unit. If no commands and synchronization commands are received at step 114, the electrode goes back to step 112 and selects another receive frequency from its list of default frequencies. If commands and synchronization data have been received, at step 116 the electrode sends is unique identification data (containing information on the position on the patient's body) on the assigned frequency and in the assigned time slot back to the base unit, indicating to the base unit that it is ready to acquire ECG signals and is in an operating condition.

In an alternative embodiment of the invention, the plurality of individual, remotely programmable wireless transceivers 20 are initially generic with respect to particular placement locations on the surface of a patient's body. Furthermore, the electrodes could be manufactured without preprogrammed functional position identifiers. This is advantageous since it would not be necessary to have the hospital or user maintain an inventory of individual electrodes based on functional position (i.e., LA, RA, LL, V1, V2, etc.). All the electrode assemblies are considered generic and could be programmed with unique identifiers indicating the position on the body by the base unit when the user sets up the ECG system. The procedure of FIG. 8 could be used for programming of each electrode when initializing the ECG system. After first time programming of the electrode assemblies, the system only needs to go through the initialization program of FIG. 6 when it is powered up again.

Figure 8:
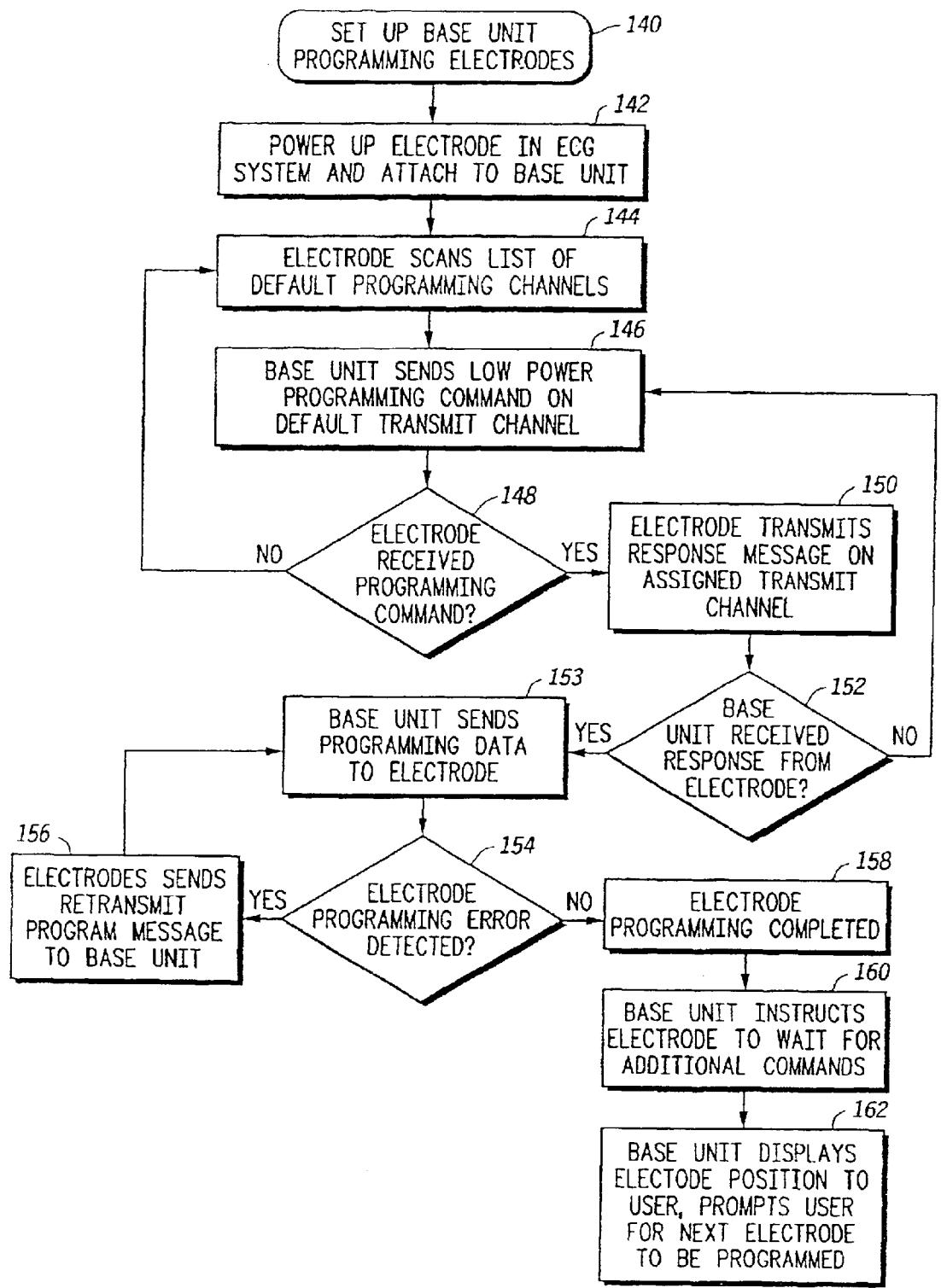
FIG. 8 is a flow diagram of a programming procedure for programming the wireless transceivers of FIG. 1 when initializing the ECG system of FIG. 1.
Figure 10:
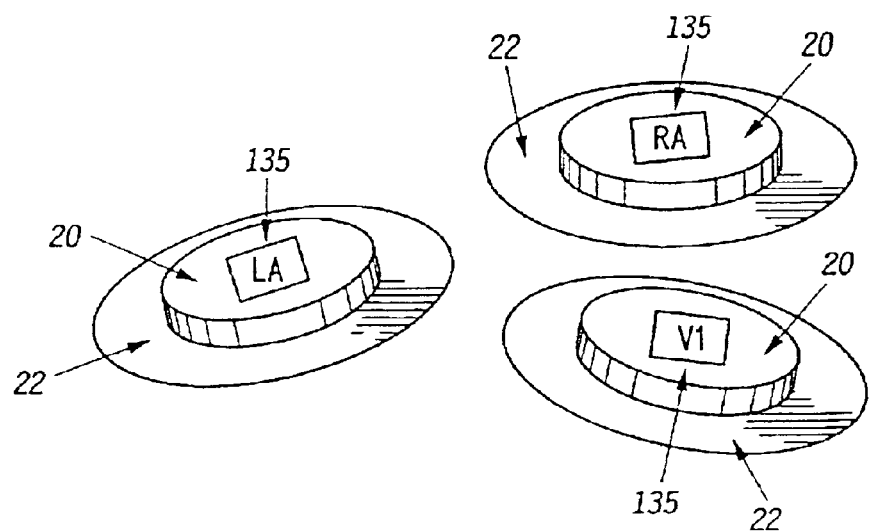
FIG. 10 is a perspective view of three wireless transmitters after the procedure of FIG. 8 has been completed.

FIG. 8 shows the initialization procedure in the alternative embodiment. FIG. 9 shows the base unit 18 having a user interface 61 comprising a display 132 and a plurality of buttons or keys 133 for assisting the user to interact with the base unit. A group of generic wireless transceivers 20 are shown ready for initialization. The user has a set of pre-printed labels 135, which are removed from a plastic backing and placed on the wireless transceivers as shown in FIG. 10.

Referring now to FIGS. 8 and 9, at step 140 the user sets up the base unit into an electrode programming mode, such as by responding to prompts on the display 132 and selecting the mode with one of the buttons or keys 133. The base unit programming mode could be done at lower power transmissions, requiring the wireless transceiver 20 to be programmed to be adjacent to the base unit (thereby avoiding programming more than one transceiver at a time). Alternatively, as shown in FIG. 9, the base unit has a programming initialization interface 136 which makes contact with a socket or other feature in the transceiver for purposes of programming the transceiver during initialization. When the transceiver is placed into contact with the programming initialization interface 136, the base unit could automatically go into programming mode, or it could simply go into programming mode upon power up.

In any event, at step 142 the first electrode assembly 20/22 is powered up and placed near the base unit or positioned in contact with the programming initialization interface 136. The initialization of the electrodes could be done by mechanical means, such as plugging the electrode transceiver 20 into the base unit programming initialization interface 136.

At step 144, the electrode scans the default programming channel. At step 146, the base unit sends a low power programming command on the default transmit channel or some other channel that has the least RF interference. At step 148, the electrode determines whether it has received the programming command. If not, the electrode scans the list of default channels and selects a new channel to listen on. If so, the electrode transmits a response message on its assigned transmit channel at step 150. At step 152, the base unit determines whether it has received the response from the electrode. If not, the base unit goes back to step 146 and transmits the low power programming command on a new transmit channel. If so, the base unit transmits programming data to the electrode at step 153. At step 153, the programming data includes the electrode unique identifier, including the electrode position (LA, RL, or V3, etc.), the base unit unique identifier, and other registration commands as described above. At step 154, the electrode determines whether a programming error was detected, and if so at step 156 sends a retransmit program message to base unit causing it to repeat the programming data at step 152. If no error occurred, the process proceeds to step 158, at which the electrode completes programming with the base unit. At step 160, the base unit instructs the electrode to wait for additional commands. At this point, since the unique base unit ID has been programmed in the wireless transceiver, it can scan ECG system control channels and receive and operate on commands only from the base unit that programmed the transceiver. At step 162, the base unit displays the electrode placement position on the user interface display and prompts the user to place the next electrode for programming into the initialization interface 136.

After all the electrodes have been programmed, the base unit will automatically be configured for the proper number of electrodes used in the ECG system. As each electrode is programmed the user removes a label 135 from the stock of labels 137 indicating the position programmed on the electrode and applies the label to the electrode (e.g., to the top or upper surface of the wireless transceiver 20), as shown in FIG. 10.

From the foregoing description, it will appreciated that we have described a dynamically programmable, wireless electrocardiograph (ECG) acquisition system, comprising: a plurality of individual, remotely programmable wireless transceivers 20, each transceiver associated with a patch electrode 22 for use in ECG monitoring, and a base unit 18 comprising a wireless transceiver 54 (FIG. 4) for sending and receiving messages to the plurality of individual transceivers 20. The base unit and wireless transceivers 22 implement a wireless programming protocol by which messages and information are exchanged between base unit 18 and wireless transceivers 20 (such as shown in FIGS. 6 and 8) whereby registration, configuration, and data transmission control properties of the wireless transceivers may be managed by the base unit.

Preferably, the base unit transmits a global time base signal to the wireless transceivers, the global time base signal synchronizing the timing of transmission of ECG signals acquired by the wireless transceivers in discrete time slots in a single frequency channel. As shown in FIGS. 1 and 4, the base unit further comprises an interface 70 to a conventional ECG monitoring equipment such as a display, whereby acquired ECG signals may be transmitted to the ECG monitoring equipment for display. The system of base unit 18 and wireless remotely programmable transceivers 20 is particularly well adapted for use with standard conventional patch electrodes and existing ECG monitoring equipment, and thus presents a flexible, low cost and convenient approach to acquiring ECG signals and presenting them to a display unit for display.

Over the Air Programming Procedures:

The system 10 of FIG. 1 utilizes over the air (OTA) programming procedures to exchange messaging and information between the base unit and electrodes (that is, the wireless transceivers 20). Various types of information could be transacted for the general purposes of registration, initialization, configuration, calibration, data acquisition control, transmission synchronization, error correction or recovery, power mode control, and auditing status.

The programming procedures described herein are based on a set of instructions that are stored in a memory in the base unit (such as memory 64 of FIG. 4), and executed by a computing platform such as the microcontroller 58 to generate commands that are transmitted via wireless communication to the plurality of wireless electrodes. Similarly, the wireless transceivers in the electrodes receive the commands from the base unit, and execute instructions stored in a memory in order to respond to the commands and transmit response messages (such as audit response messages etc.) back to the base unit. The following is a description of these instructions. Preferred embodiments of such procedures (i.e., sets of instructions) are described below in conjunction with FIGS. 11–30:

a. Configuration of data acquisition sampling rate procedure. Variable sampling data rates could be set to accommodate varying physiologic signals (ECG, EMG, EEG, etc.). The sampling rates will differ according to the nature of frequencies evoked in such physiologic events. Also, certain application needs for specialized tests within a specific area may require faster sampling rates.

Figure 11:
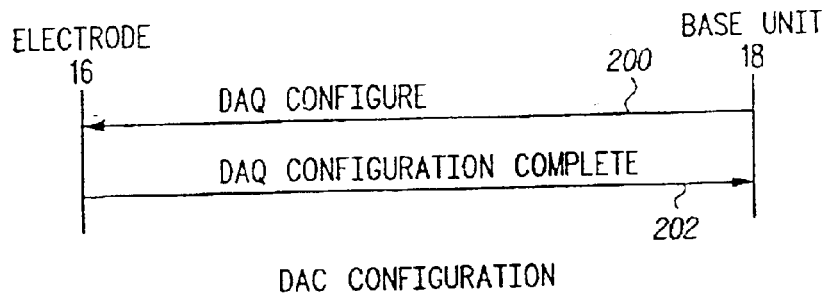
FIGS. 11–26 are illustration of the message flow between the base unit and the electrode assemblies during various different programming procedures according to a preferred embodiment of the invention.

The programming procedure of FIG. 11 is employed to configure the data acquisition sampling rate. The base unit 18 sends a data acquisition configuration message 200 to the electrode assembly 16 (i.e., wireless transceiver 20). The message contains data identifying a sampling rate for the wireless transceiver's A/D converter. When the message 200 is received by the wireless transceiver and processed in the microcontroller, the sampling rate for the A/D converter is changed. The wireless transceiver sends back a data acquisition configuration complete message 202 indicating that the change is data sampling rate was accomplished.

b. Configuration of amplifier gain setting procedure. Variable signal preamplification gain (prior to digitization) could be set to accommodate and correct for weak biopotential signal strength at the skin surface, or a bad surface connection, as well as changes in skin resistance due to dry or humid environmental conditions and temperature changes. The signal amplification gain factor could be adjusted dynamically until a reasonable signal strength is obtained. Typically, ECG signals re in the 1–5 mV range, while EEG signals are in the 1–100 $\mu$V range. Different gain selection is desirable to obtain the sensitivity that is needed for the specific application.

Figure 12:
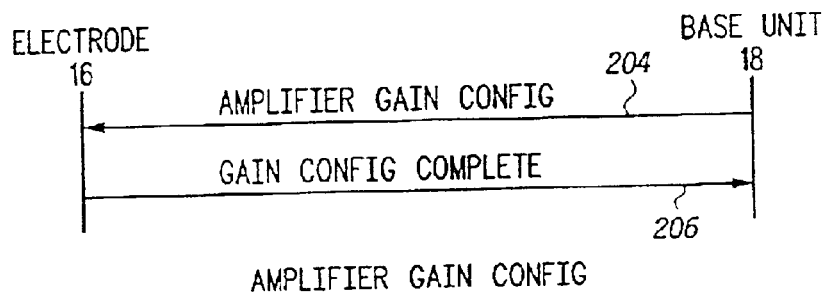
Figure 13:
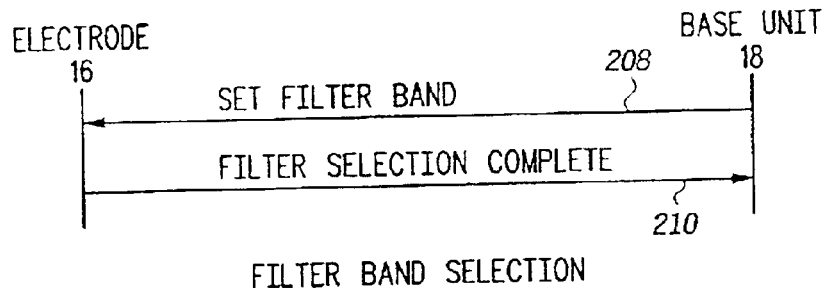

When the base unit determines that the amplifier gain needs to be adjusted, the procedure of FIG. 12 is used. The base unit sends an amplifier gain configuration message 204 to the electrode 16's wireless transceiver 20 (FIG. 3). The microcontroller 32 processes the message and adjusts the gain setting to the amplifier 30 providing an analog signal to the A/D converter 32 of FIG. 3. When the gain has been adjusted, the transceiver sends a gain configuration complete message 206 back to the base unit.

c. Configuration of pre-amplifier (anti-aliasing) filter band settings procedure. Flexibility of adaptation of the monitoring system 10 to variable application needs may require a dynamic re-selection of an anti-aliasing filter band in the preamplifier of the wireless transceiver. An optimal filter can be selected from a bank of filters preset at different frequency bands to filter out noise or unwanted artifacts. The programming procedure of FIG. 13 is employed. The base unit sends a set filter band message 208 identifying the frequency band (or filter) for the anti-aliasing filter (not shown) in the analog signal path in the wireless transceiver.

d. Configuration of carrier channel setting procedure. In order to allow multiple users of monitoring systems to co-exist in same physical area, and at the same time reduce the possibility of interference, a multi-frequency channel system is implemented to eliminate the possibility of interference in communications between the base unit 18 and the wireless transceivers of any given system 10. The base unit 18 dynamically detects interference by listening to a specific frequency channel during configuration, such as a default frequency channel, and determines the suitability of use for the monitoring system based on noise levels in that frequency channel. The base unit 18 can also apply this procedure if too many errors were encountered during the decoding of signaling received on a specific channel due to increasing noise, or during system reset and reconfiguration procedures.

Figure 14:
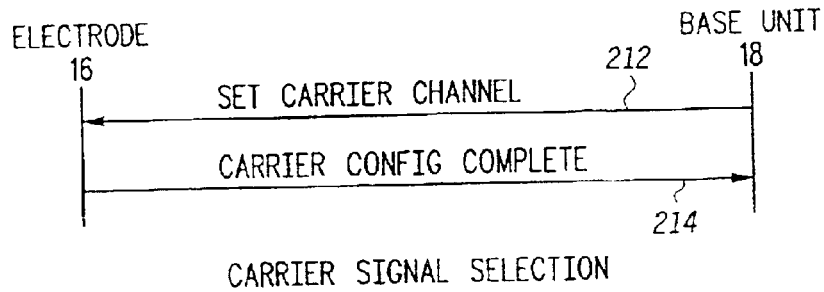
Figure 15:
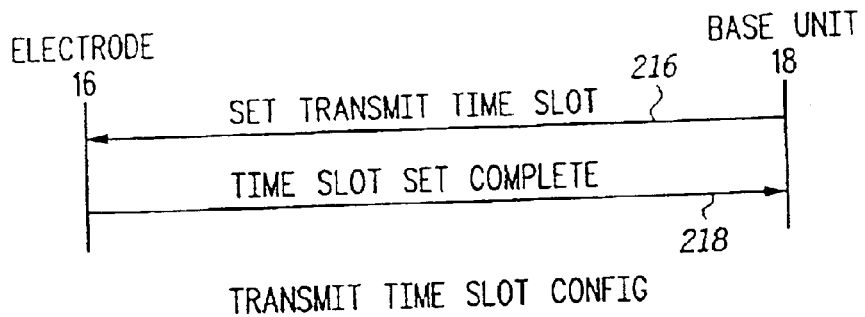
Figure 16:
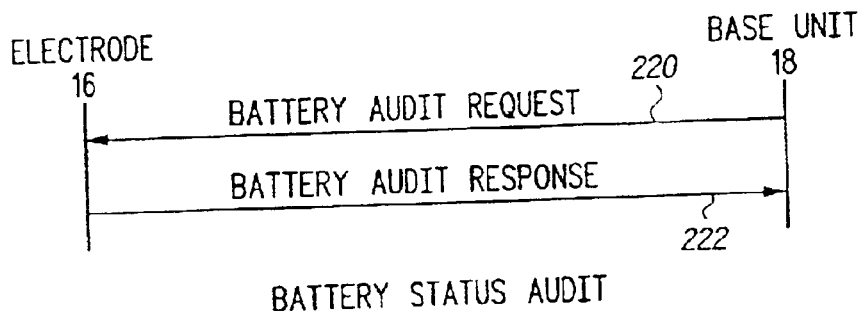
Figure 17:
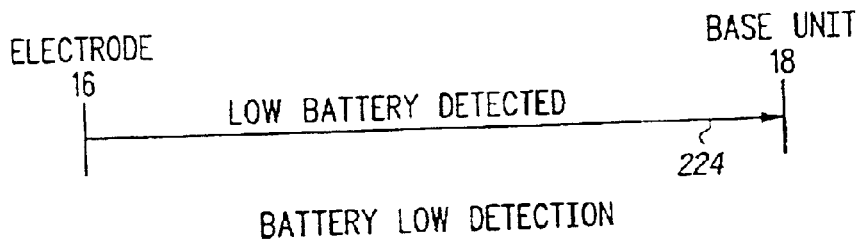
Figure 18:
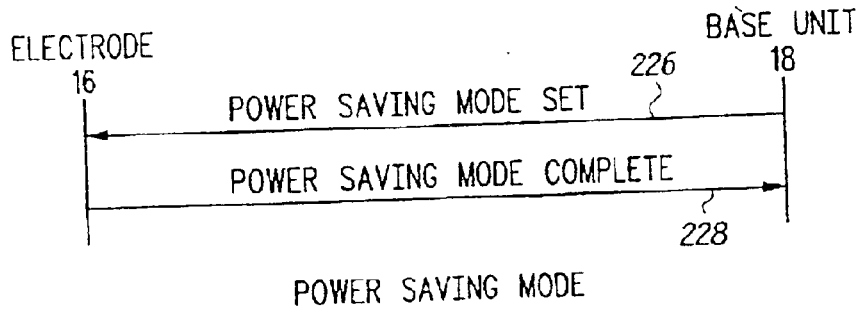
Figure 19:
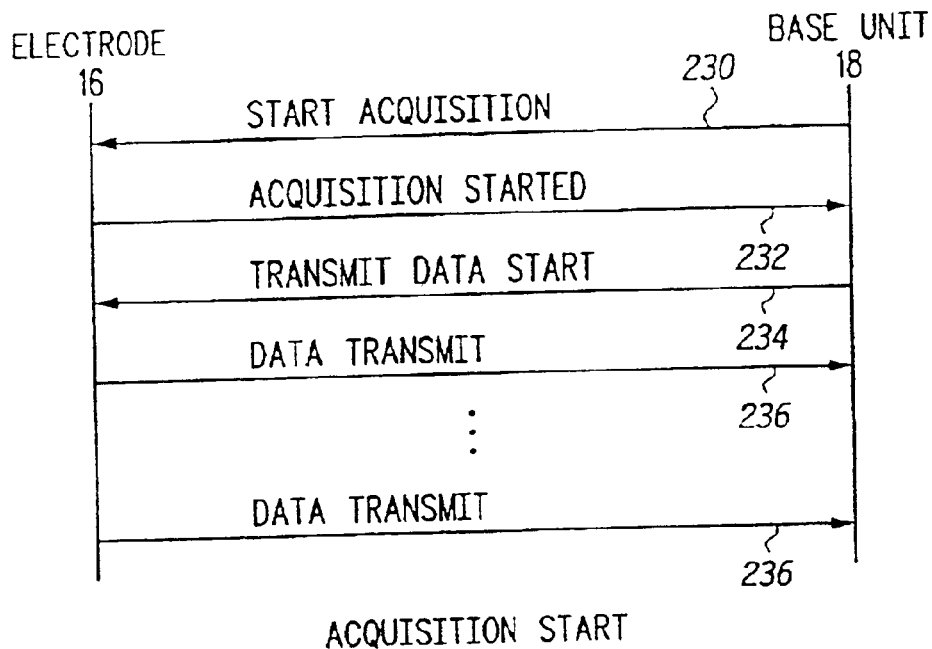
Figure 20:
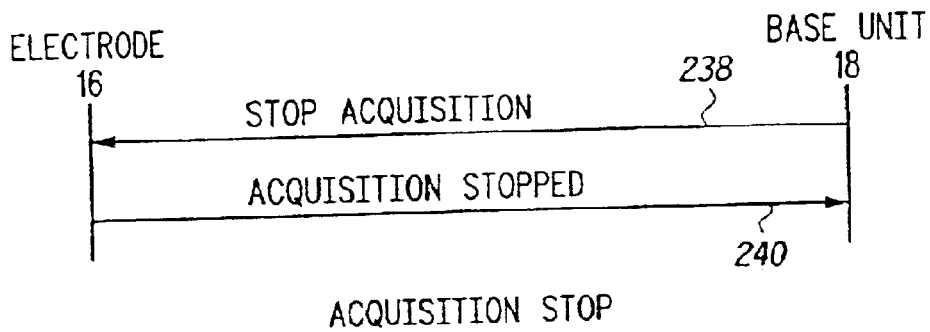
Figure 21:
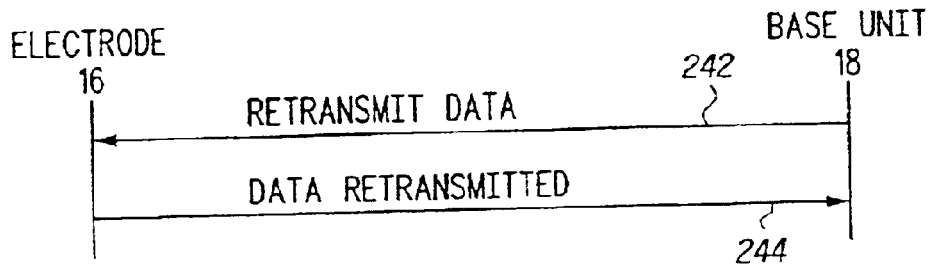
Figure 22:
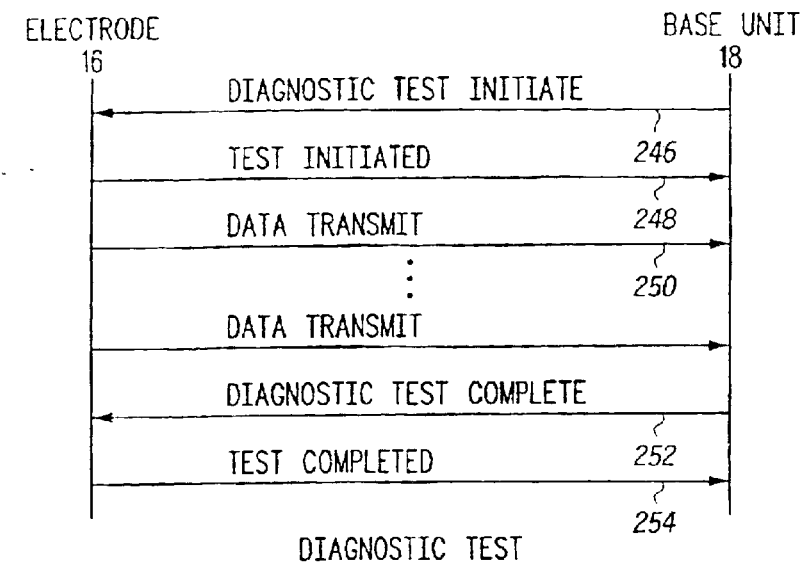
Figure 23:
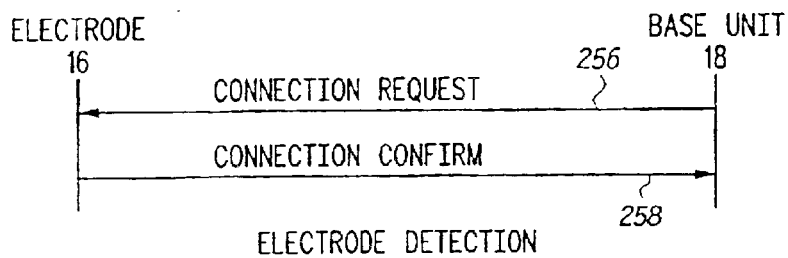
Figure 24:
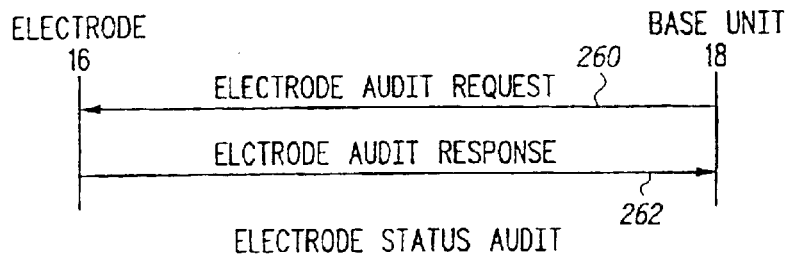
Figure 25:
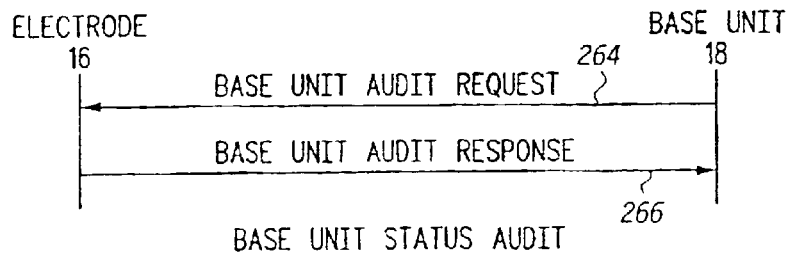
Figure 26:
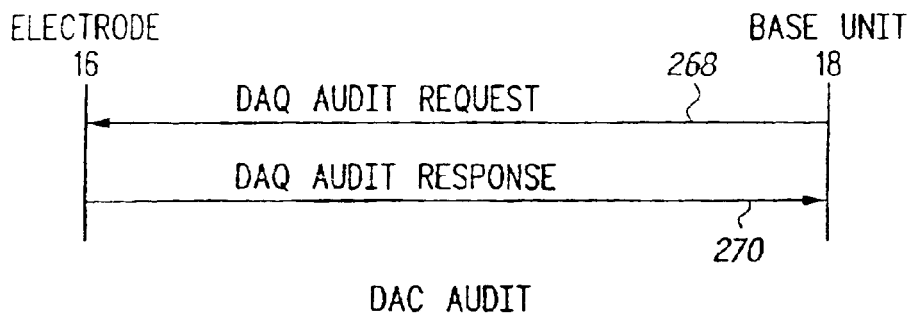
Figure 27:
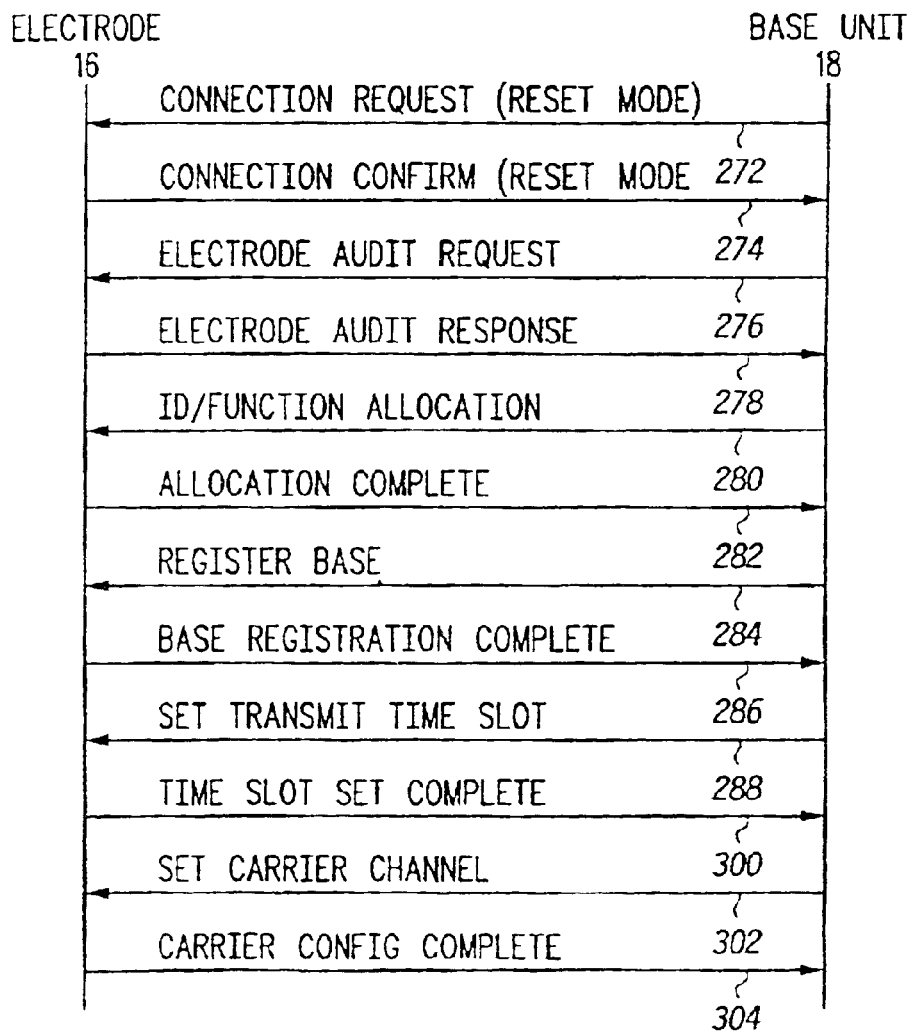
FIG. 27 is an illustration of a registration procedure by which the base unit is registered with the electrode assemblies.

The procedure of FIG. 14 is employed for carrier channel setting changes. The base unit sends a set carrier channel message 212 to the electrode. The message 212 identifies the new carrier channel. The wireless transceiver's frequency generator is responsively adjusted to generate a carrier signal at the new frequency. When the configuration is complete, the electrode sends a carrier configuration complete message 214 back to the base unit.

e. Configuration of timing signal for transmission time slot procedure. The procedure of FIG. 15 sets the assignment of a specific time slot for each wireless transceiver (in a time division multiple access (TDMA)-based system) for transmitting and/or receiving data between the electrode's wireless transceiver 20 and the base unit 18. Such synchronization is necessary in a TDMA-based system to allow multiple electrodes transmitting on the same frequency channel to relay their information to the base unit without interfering with one another. The procedure consists of the base unit sending a set time slot message 216 to the electrode, identifying a particular time slot for each electrode. When the electrode has set the time slot, it sends back a time slot set complete message 218.

f. Battery utilization sleep/activation mode procedure. The battery utilization sleep mode procedure of FIG. 16 will be used during shut-down process for conservation of battery power. This can also be initiated if signal communication is lost between the electrodes and the base unit, or on command from the base unit. Battery utilization activation mode will be initiated as soon as communication with the electrodes is resumed or during initialization of registration of new electrodes. The procedure involves the base unit sending a battery audit request message 220 to the electrode. The message 220 basically asks the electrode to provide battery life and current battery mode information. This information is provided back to the base unit in a battery audit response message 222.

g. Battery low voltage level detection procedure. A battery status audit procedure shown in FIG. 17 is for a condition of low battery voltage in the wireless transceiver 20 to be detected by the base unit. The procedure allows the base unit to warn the user for replacing or recharging that electrode battery. When the voltage of battery 46 of FIG. 3 goes below a threshold level (as monitored by the microcontroller), the electrode sends a low battery detected message 224 to the base unit.

h. Power Saving Mode Setting. The procedure shown in FIG. 18 allows the base unit to change the power saving mode of the wireless transceivers to conserve battery life and be more economical. Different levels of power saving modes can be selected based on the needs of the operation. A memory retention sleep mode can also be implemented in the wireless transceiver. The system can also have a wake up timer or change to active mode at the command of the base unit. The procedure involves the base unit sends a power saving mode set command 226 to the base unit. The electrode responsively changes the state of the battery 46 to a sleep or power saving mode, and when that is accomplished sends back a power saving mode complete message 228 back to the base unit.

i. Acquisition start/stop procedure. The procedure of FIG. 19 allows the base unit to command the electrodes to start the data acquisition and transmit the data to the base unit, or stop the data acquisition process. Multiple start/stop messages of the type shown in FIG. 19 may be needed to interrupt a continuous data streaming of information to the base unit in the event of reconfiguration, a frequency channel reselection is needed due to interference, or when power saving (sleep) mode is requested. Other situations are possible. The procedure begins. by the base unit sending a start data acquisition message 230 to the electrodes. The electrodes acknowledge the start of data acquisition with a acquisition started message 232. The base unit then commands the electrode to start transmission of data by message 234. The data is sent from the electrodes as indicated by data transfer messages 236. In this illustrated embodiment, this is by time division multiplexing on a single carrier frequency in time slots and by frequency as provided in FIGS. 14 and 15.

j. Data transmit procedure. Once data acquisition is started, data is transmitted from each of the electrodes to the base unit in either a synchronous or an asynchronous manner. This is shown in FIG. 19. At the base unit, data is decoded, collected, buffered, and checked for error occurrence during transmission. Base unit 18 also controls the stoppage of data transmission, as shown in FIG. 20. This procedure involves the base unit sending a stop acquisition message 238. The electrode ceases data acquisition and transmission and sends an acquisition stopped message 240 back to the base unit.

k. Error sample data recover/retransmit procedure. In the event of an error occurring during transmission of the data from the electrodes to the base unit, the data can be requested for re-transmission. This procedure is shown in FIG. 21. The base units sends a retransmit data message 242 to the electrode. In response, the electrode retransmits stored data stored in the memory 36, as indicated at 244. The electrode should have a minimal buffer storage of the previous data collected in buffer 38 in the event error recovery is needed due to a noisy or bad signal transmission.

l. System test diagnostic procedure. The procedure of FIG. 22 instructs the electrodes to transmit a diagnostic test data pattern in order to analyze the system for optimal performance. Also, it may be used to resolve issues in local ground referencing across all electrodes for calibration purposes. A diagnostic test initiate message 246 is sent from the base unit to the electrode. Receipt of the message 246 causes the microcontroller to initiate certain tests or transmit a diagnostic test pattern according to a set of instructions or code stored in the memory 68 designed to respond to the message 246. A test initiated message 248 is sent back to the base unit, acknowledging the message 246. After the test is performed, test data is transmitted to the base unit as indicated at 250. When all of the test data has been received, the base unit sends a test complete message 252 to the electrode, and the message is acknowledged by a test completed message 254.

m. Scan of electrode current channel setting procedure. A procedure may be implemented to allow the base unit to scan for an electrode that is transmitting on an unknown frequency channel. Using a signal strength indicator, the specific transmission channel can be determined. The electrode can be reconfigured to transmit on a new channel using the procedure of FIG. 14.

n. Electrode detection procedure. The procedure of FIG. 23 is initiated periodically, as a means of providing a continuous search and "keep-alive" signal. The electrode detection procedure involves a connection message 256 that is transmitted from the base unit to the electrodes. The electrodes respond with a connection confirm message 258 which tells the base unit that the electrode is "alive". If this electrode detection message 256 is not received periodically by the electrodes, then they stop data acquisition and move into a power saving mode. The signaling can be done on an interval basis (e.g., every 30 seconds) and on the last previously selected traffic channel.

o. Electrode Status Audit: A procedure shown in FIG. 24 allow the electrode status to be audited by the base unit when needed to ensure proper operating conditions and configuration parameters. The procedure involves the base unit sending an electrode audit request message 260. The electrode responds to the audit message with an audit response message 262 indicating current operating conditions and configuration parameters, e.g., gain setting, preamplification filter band, reference signal, time slot, carrier frequency, data acquisition rate, serial number, etc.

p. Base Unit Audit. Referring to FIG. 25, a base unit's status can be audited by the electrodes when needed to ensure proper operating conditions and configuration parameters. The electrodes send a base unit audit request message 264 to the base unit and it responds with an audit message 266 indicating its current configuration parameters, such as channel frequency.

q. Data acquisition subsystem audit. Referring to FIG. 26, the data acquisition subsystem in the wireless transceivers, consisting of the preamplifier, amplifier and D/A converter, can be individually audited for proper operation status and configuration settings. The base unit sends a data acquisition (DAQ) audit request message 268 to the electrode and the information is provided in a DAQ audit response message 250.

System Operation Procedures:

a. Registration of electrodes with the base unit. A preferred registration procedure includes (but is not limited to)

detection of electrode type and identifier. The patient reference number and/or demographics can also be stored in each electrode so they are associated uniquely with a specific patient. Assignment of electrode function (anatomical or functional position) in this monitoring system is also performed. Assignment of any temporary identifiers to the electrodes can also be performed. The registration procedure can be initiated on a dedicated frequency control channel(s) for initialization. The registration procedures of FIGS. 6 and 8 are one possible embodiment of the registration procedure. Another possible embodiment in shown in FIG. 27. The base unit sends a connection request message 272 to the electrodes. The electrodes reply with a connection confirm message 274. This is the procedure of FIG. 23 described previously. Then electrode audit messages 276 and 278 are exchanged, the procedure of FIG. 25. The base unit sends a n ID/Function allocation message 280 that assigns the electrode with a temporary ID and body position or function. The electrode sends an allocation complete message 282 in response to the allocation message 280. A base unit registration message 284 is sent to the electrode, registering the electrode with the base and conveying the base unit identification to the electrode. A base unit registration complete message 286 is sent in response. Messages 288, 300, 302 and 304 assign the time slot and carrier channel for the electrode, implementing the procedures of FIGS. 14 and 15.

b. Registration of the base unit with the electrodes. A registration procedure may be implemented by which the base unit registers with the electrodes is also performed. The procedure is shown in messages 284 and 286 of FIG. 27. The procedure includes the detection of a base unit type and an identifier associated with the base unit. The messages 284 and 286 of FIG. 27 serves to restrict electrodes to accept communication from only a single base unit. The registration procedure can be initiated on a dedicated frequency channel(s) for initialization.

c. Total signal loss recovery scenario. A procedure shown in FIG. 28 is provided which recovers from a total loss of signal from one or more of the electrodes. The procedure is initiated in the event of weakening transmission signal strength due to fading channels, or low available transmission power, or large physical distance between the electrodes and the base unit. A continuous search and "keep-alive" signal is transmitted from the base unit to the electrodes. Once an electrode is detected, communication is re-established, and the base unit resumes collection of the data. The procedure begins with the connection request and confirm messages 306 and 308 (the procedure of FIG. 23 described previously), the electrode audit messages 310 and 312 (the procedure of FIG. 24), and the data acquisition subsystem audit messages 314 and 314 (the procedure of FIG. 26). Depending on the response to the audit messages, the base unit may initiate any number of configuration commands to restore the electrode to a proper operating condition, such as the DAQ configure message 316 which configures the data acquisition subsystem in the wireless transceiver. The electrode sends the complete message 318 when the subsystem has been reconfigured in accordance with the settings contained in the message 316. As another alternative, the set carrier channel messages 320 and 322 can be exchanged (the procedure of FIG. 14). As another alternative, a diagnostic test can be initiated as indicated by messages 324, 326, 328, 330, 332 and 334, implementing the procedure of FIG. 22 described above. Additionally, amplifier gain can be configured by messages 338 and 334 (the procedure of FIG. 12). Any or all of the messages shown in dashed lines could be implemented. After a successful reconfiguration of the electrode, data acquisition and transmission is reestablished by messages 340, 342, 344 and 346, namely the procedure of FIG. 19 described above.

d. Monitoring system configuration scenario: A procedure shown in FIG. 29 is provided for the overall monitoring system configuration. The system 10 will set up and configure multiple subsystems including: data acquisition, filtering and signal conditioning, amplifier gain setting, and run diagnostic tests to ensure quality of transmitted data. The configuration begins by a connection request message and response connection confirm message 350 (the procedure of FIG. 23), the data acquisition subsystem audit messages 352 and 354 (the procedure of FIG. 26), the data acquisition subsystem configuration messages 356 and 358, and the setting of the preamplifier filter band by messages 360 and 362 (the procedure of FIG. 13). Then a diagnostic test procedure consisting of messages 362, 364, 366, 368, 370, 372, and 374 are exchanged, implementing the procedure of FIG. 22. An optional amplifier configuration command can be send as message 376 depending on the results of the diagnostic test just performed. When the amplifier gain is successfully changed the gain configuration complete message 378 is sent back to the base unit.

e. Monitoring system data acquisition start scenario: The system will start the data acquisition and transmission through the traffic channel to the base unit once system configuration is complete. The procedure of FIG. 30 shows one possible embodiment. A configuration request message 380 is sent, generating the configuration confirm message 382 from the electrode (procedure of FIG. 23). Data acquisition start messages 384 and 386 are exchanged (procedure of FIG. 19). Acquired data is transmitted via messages 388 and 390. Depending on the signal strength and error detection, the gain of the amplifier 30 in the wireless transceiver can be adjusted via amplifier gain configuration message 392 and when the change is made a gain configuration complete message 394 is sent back to the base unit.

Wireless Electrode State Machine

Figure 31:
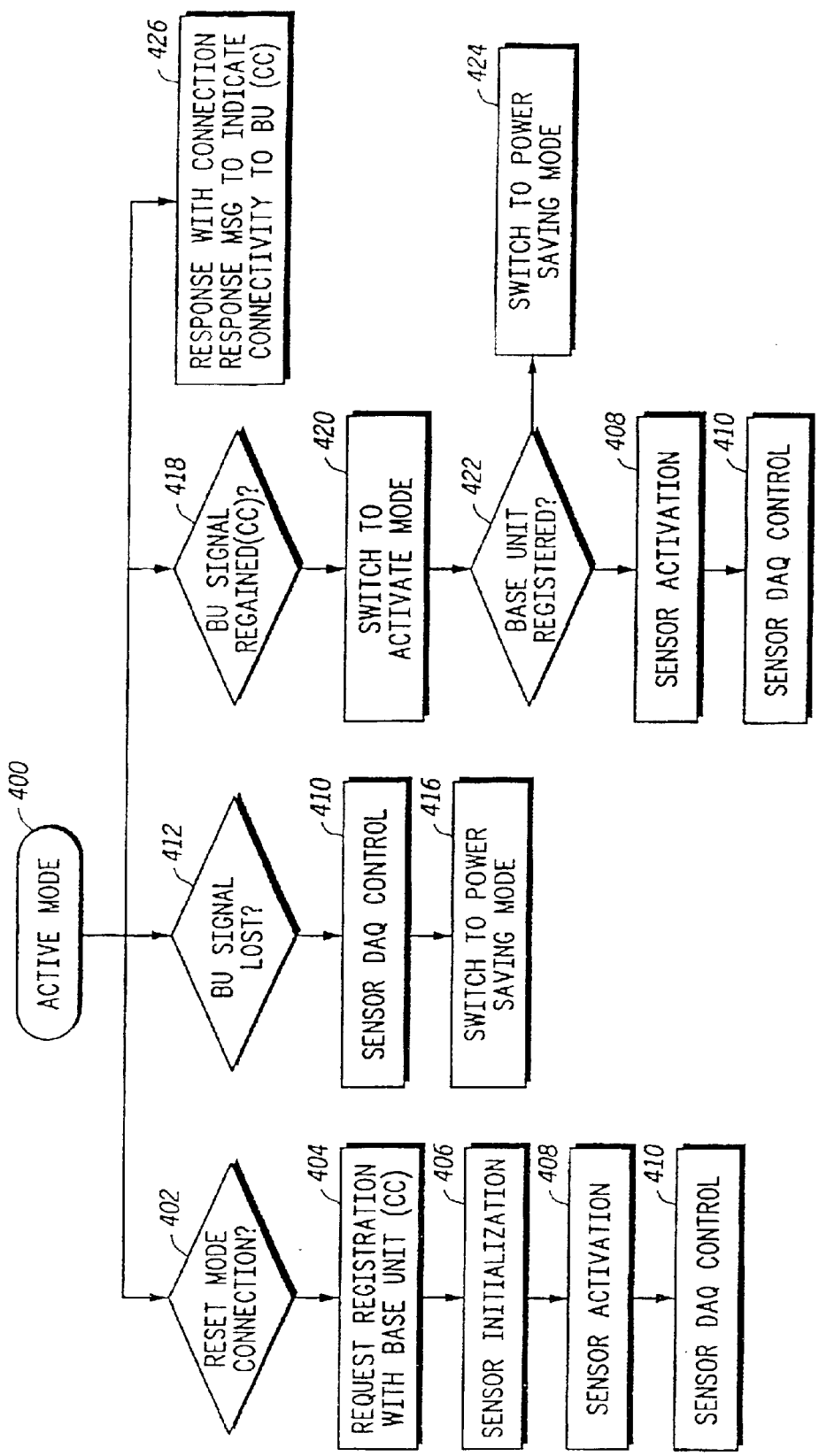
FIG. 31 is a logic diagram representing a state machine and software modules in the wireless electrode transceiver assemblies.
Figure 33:
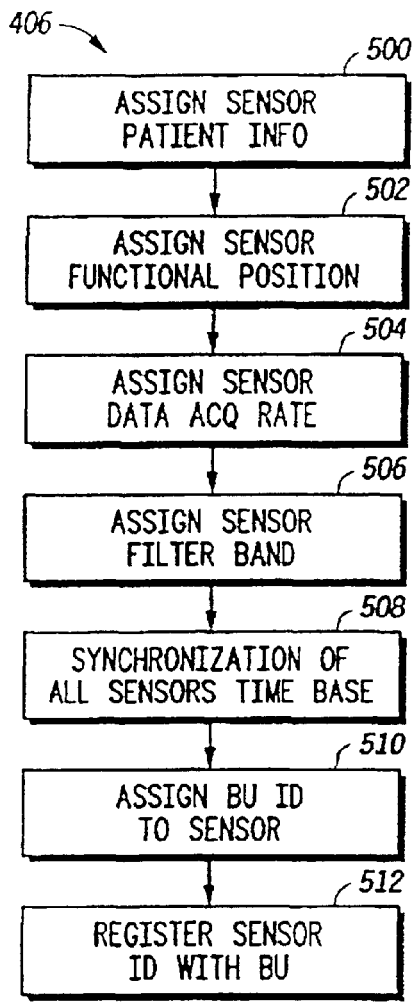
FIG. 33 is a diagram of a electrode initialization with reset connection routine shown in FIG. 32.

FIG. 31 is a logic diagram for a state machine running in the microcontroller/DSP computing platform in the wireless electrode transceiver assembly 20 of FIGS. 2 and 3. When the device is powered up and running (and acquiring biopotential signals), the state machine is in an active mode 400. The state machine reacts to conditions that may be present, and responds to those conditions as shown in the figure. If the user plugs the transceiver assembly into the programming pin or interface on the base unit, the state machine goes into a reset mode connection state 402. This event prompts initiation of a set of routines that request registration with the base unit, as shown in 404. After registration procedures are accomplished (described elsewhere in this document), a sensor initialization routine 406 is entered. The routine 406 is shown in FIG. 33 and described subsequently. Then, a sensor activation routine 408 is entered, shown in FIG. 34. Finally a sensor data acquisition subsystem (DAQ) control routine 410 is entered, shown in FIG. 35.

Another event that triggers exit of the active mode state is when the base unit's "keep alive" or connection request signal is lost, as indicated at 412. This may occur for example when the patient moves out of range of the base unit temporarily or a problem occurs with the base unit.

When this occurs, the microcontroller enters the sensor DAQ control routine 410 and stops the acquisition of data. (This assumes that the memory size of the memory in the transceiver assembly 20 is too small to store significant amounts of data while contact with the base unit is interrupted; if sufficient memory capacity is present, the data could continued to be acquired and stored locally in the memory). The battery 45 is then switched to a power saving mode as indicated by routine 416.

Figure 34:
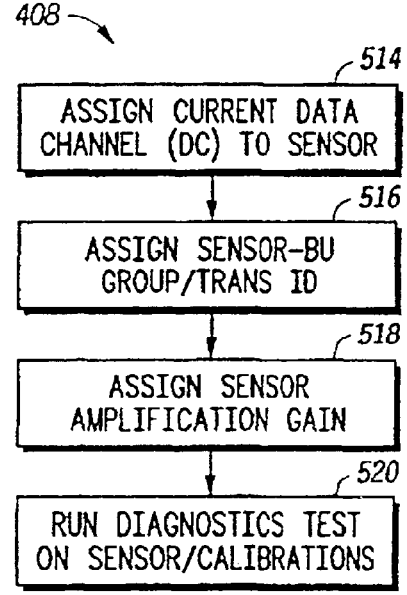
FIG. 34 is a diagram of an electrode activation routine shown in FIG. 32.

Another event that can occur is the base unit's signal is regained as indicated by condition 418. When this occurs, the state machine returns to active mode 400, as indicated by routine 420. The wireless transceiver assembly enters a base unit registration procedure 422, wherein the transceiver assembly re-registers with the base unit. If the base unit it is attempting to register is not its original base unit (for example where the base unit's ID is different from the original base unit ID), then a routine 424 is entered in which the battery is switched to power savings mode. If the base unit is the original base unit, the sensor activation and data acquisition subsystem routines 408 and 410 of FIG. 33 and FIG. 34 are entered.

While the electrode is in the active mode 400 state, it will normally be receiving the periodic connection request "keep alive" messages from the base unit. It will issue responses to those connection request messages periodically, as indicated by a connection request response routine 426.

Figure 32:
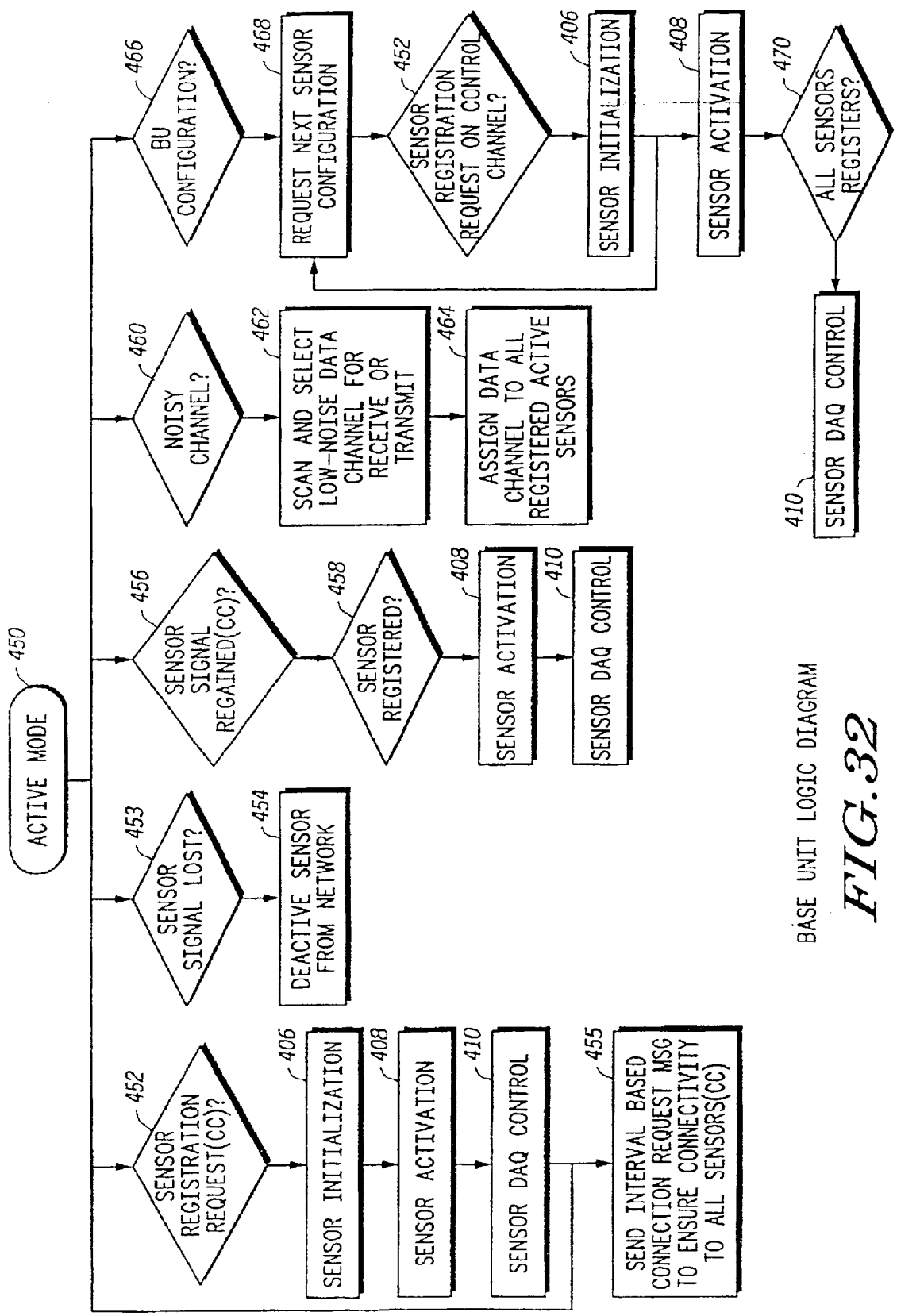
FIG. 32 is a logic diagram representing a state machine and software modules in the base unit.

FIG. 32 is a logic diagram of a base unit state machine. The state machine for the base unit also includes an active mode 450. The base machine will respond to conditions including a sensor registration request condition 452. This condition may be entered during data acquisition or during initialization. The base unit responds to this condition by entering the sensor initialization, activation and sensor DAQ control routines 406, 408 and 410. After the registration is complete, the base unit sends a connection request message to all registered wireless transceiver assemblies to insure that they are still operational and within RF range of the base unit, as indicated at 454.

If the signal from one of the wireless transceiver assemblies is lost, as indicated by condition 453, then the sensor is deactivated from the system as indicated by 454. This step may be accompanied by an alarm or message on the user interface of the base unit.

If the signal is regained, as indicated by condition 456, a sensor registered routine 458 is entered to insure that the signal that is received originates from a registered transmitter assembly. Then, the sensor activation and DAQ control routines 408 and 410 are entered.

Another condition that can occur is a noisy uplink or downlink channel, represented by 460. When this occurs, the base unit enters a routine 462 in which available uplink or downlink channels are scanned and a low-noise channel is selected. Then, a routine 464 is entered in which the new channel is assigned to all the registered and active wireless transceiver assemblies.

Another event that can occur is a base unit configuration 466, which can occur in response to a prompt from a user. When this condition occurs, the state machine enters a routine 4678 that prompts the user to enter the configuration information for the next wireless transceiver assembly. The sensor registration request routine 452 is transmitted to the wireless transceiver assembly on the control channel or via the programming interface. Sensor initialization and activation routines 406 and 410 are then entered. If more transceiver assemblies are to be programmed, the process returns to step 468. If all of the assemblies have been programmed and registered, as indicated by routine 470, then the system will enter a sensor DAQ control routine 410 to start data acquisition and transmission, either automatically or in response to input from the user at the base unit user interface.

FIG. 33 is a illustration of the sensor initialization routine 406 of FIG. 31. The routine consists of a subroutine 500 that assigns a patient ID to the transceiver assembly. Next, a subroutine 502 is entered in which the functional position of the transceiver assembly is assigned by the base unit in response to user prompts. A sensor data acquisition rate assignment subroutine 504 is then entered. The anti-aliasing filter band is assigned by subroutine 506. Then the transceiver assemblies are synchronized by a global time base signal that is broadcast on the downlink channel in subroutine 508. Then, the base unit ID is assigned to the transceiver assemblies by subroutine 510 and the electrode ID values are registered with the base unit in subroutine 512. The order of execution of modules 500, 502, 504, 506, 508, 510 and 512 is not critical.

FIG. 34 illustrates the sensor activation routine 408 of FIGS. 31 and 32. This routine includes a subroutine 514 that assigns the current data channel to the wireless transceiver assemblies. A subroutine 516 assigns a sensor-base unit group/transmission ID for each of the wireless transceivers. Transceiver amplification gain is assigned in subroutine 518. Then, a subroutine 520 is entered that runs diagnostic tests on the wireless transceiver assemblies and calibrates the units accordingly.

Figure 35:
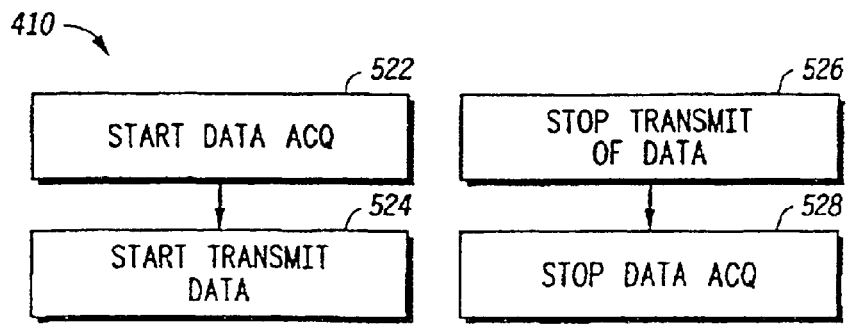
FIG. 35 is a diagram of electrode data acquisition and transmission control routines of FIG. 32.

The sensor data acquisition control routine 410 is shown in FIG. 35. This routine consists of two parts, a start data acquisition subroutine and a stop data acquisition subroutine. The start data acquisition subroutine includes a first module 522 that sends a command to the registered wireless transceiver assemblies to start data acquisition, and a second module 524 that commands the assemblies to start data transmission. The stop transmit of data subroutine includes a first module 526 that commands the wireless transceiver to stop transmission of data, and a second module 528 that commands the data acquisition subsystem to stop acquiring data.

Electrode System Initialization/Operations Management

The following is a pseudocode listing of system initialization and operations management routines for the base unit and the electrodes, as an alternative embodiment to the procedures of FIGS. 6 and 8.

Electrode power up/reactivation (battery attachment)
    If no pre-stored channels is selected (first-time power up)
        or connection is in reset mode
        Electrodes scan pre-set dedicated channel(s) for input
            signaling from base unit.
    Else
        Start using pre-stored temporary transmit and receive
            channels for messaging.
    End
Base Unit power up—reactivation
    If no pre-stored channels are selected, or reset mode
        connection is requested, or current traffic
    Channel interference is high
        Base Unit scans and selects a low-noise temporary
            transmit traffic channel for all electrodes to transmit
            signaling on.
        Base Unit scans and selects a low-noise temporary
            receive traffic channel for all electrodes to receive
            signaling on.

Else
    Use previously stored transmit and receive channels
End
Base Unit periodically transmits signaling on pre-set dedicated channel(s) if electrode is not registered or disconnected, and listens (scans) for electrode response. All other transmission occurs on temporary traffic channels.
    Send "keep-alive" signaling and scan for response from an electrode, then
        For each electrode required for current configuration settings, once detected (connection established)
        Electrode is assigned a temporary identifier.
        Electrode is associated with patient demographics info.
        Electrode is assigned a functional or anatomic position in the monitoring system.
        Electrode is requested to move to a new temporary transmit traffic frequency channel and time slot.
        Electrode is requested to move to a new temporary receive traffic frequency channel (and time slot if any).
    End
End
If all required electrodes are registered and connected
    Electrodes are assigned a (default/selected) data acquisition rate.
    Electrodes are assigned a (default/selected) amplification gain setting.
    Electrodes are assigned a (default/selected) filter band setting.
    Run diagnostic system test to ensure quality of recordings
        Adjust amplification gain on electrodes until suitable signal strength is obtained.
        Adjust filter selection until good signal/noise ratio is obtained.
        Run synchronization tests to ensure system is properly synchronized for transfer of data test patterns.
    End
    Start data acquisition and monitoring.
End
Base Unit may do any of the following during operation monitoring
    Monitors and tracks for interference and bit error rate on current channel setting, if too many errors
        request retransmission of data in error due to interference, or if too many errors then
        select and move to new temporary transmit and/or receive channels,
    Stops/restarts data acquisition for measured signals.
    Senses signal strength and re-adjust signal amplification gain dynamically to enable good resolution on the A/D channels.
    Interrupts data acquisition for reconfiguration or re-initialization procedures.
    Switches electrode(s) into power saving mode or reactivates electrode(s) operation.

Persons skilled in the art will appreciate that the details of the presently preferred embodiment described herein can be changed and modified without departure from the spirit and scope of the invention. The system 10 is readily adapted to acquiring other types of physiologic, chemical, physical or electrical processes, such as temperature, blood pressure, glucose, respiratory parameters, etc. The wireless sensors could be either placed on the patient's body or implanted. In this case, the wireless transceiver may connect to a different type of physiologic sensor which converts a measured parameter to a voltage (or this functionality could be incorporated in the wireless transceiver assembly) and transmits the signal to a base unit. This true spirit and scope is to be determined by reference to the appended claims.

We claim:

1. A wireless electrocardiogram data acquisition system, comprising:

a set of wireless electrodes for attachment to a patient's body, each of said wireless electrodes coupled to a transceiver assembly for transmitting and receiving wireless communications;

a base unit comprising a wireless transceiver for transmitting and receiving wireless communications with said transceiver assemblies, said wireless communications including a set of commands for said transceiver assemblies;

said base unit further comprising a memory and computing platform executing a set of instructions wherein said base unit may issue said commands to individual ones of said transceiver assemblies in response to the execution of said instructions;

each of said transceiver assemblies further comprising a memory and a computing platform for responding to said commands in accordance with instructions stored in said memory in said transceiver assembly, wherein said commands from said base unit and responses to said commands from said transceiver assemblies allow said base unit to remotely and individually manage and configure each of said transceiver assemblies in real time either prior to or during a period of time in which said transceiver assemblies are acquiring physiologic electrocardiogram signals from said patient and transmitting data corresponding to said physiologic electrocardiogram signals to said base unit.

2. The system of claim 1, wherein said commands comprise a data acquisition sampling rate command, and wherein said transceiver assemblies configure circuitry in said transceiver assembly sampling data acquired from said wireless electrode in response to said data acquisition sampling rate command.

3. The improvement of claim 1, wherein said command comprises an amplifier gain configuration command, and wherein said transceiver assemblies adjusts the gain in an amplifier in said transceiver assembly in response to said amplifier gain configuration command.

4. The system of claim 1, wherein said command comprises a filter band selection command, and wherein each of said transceiver assemblies selects an anti-aliasing filter in said transceiver assembly in response to said filter band selection command.

5. The system of claim 1, wherein said command comprises a carrier signal selection command, and wherein each of said transceiver assemblies selects a carrier frequency for transmission of said data from said transceiver assembly to said base unit in response to said carrier signal selection command.

6. The system of claim 1, wherein said command comprises a transmit time slot configuration command assigning a time slot in a time division multiplexed data transmission format during which each of said transceiver assemblies is to transmit said data to said base unit, and wherein each of said transceiver assemblies selects a different time slot in response to said transmit time slot configuration command.

7. The system of claim 1, wherein said command comprises a battery status audit command, and wherein each of said transceiver assemblies provides battery status information to said base unit in response to said battery status audit command.

8. The system of claim 1, wherein said transceiver assembly further comprises a battery and wherein each of said transceiver assemblies sends a low battery detection message to said base unit when the level in said battery falls to a predetermined threshold.

9. The system of claim 1, wherein said command comprises a power saving mode command, and wherein said transceiver assemblies change a state of battery consumption in said transceiver assembly to a power saving mode in response to said power saving mode command.

10. The system of claim 1, wherein said command comprises a start data acquisition command, and wherein said transceiver assembly begins to acquire physiologic data from said patient in response to said start data acquisition command.

11. The system of claim 1, wherein said command comprises a start data transmission command, and wherein said transceiver assemblies commences transmission of said data to said base unit in response to said start data transmission command.

12. The system of claim 1, wherein said data is transmitted to said base unit in time slots and in a frequency channel assigned to said transceiver assembly from said base unit.

13. The system of claim 1, wherein said base unit conducts error checking of said data transmitted from said transceiver assemblies, and wherein said base unit issues a retransmit data command to said transceiver assemblies, said transceiver assemblies retransmitting data previously transmitted to said base unit in response to said retransmit data command.

14. The system of claim 1, wherein said command comprises a diagnostic test initiation command, said transceiver assemblies commencing a predetermined diagnostic test routine and sending diagnostic test data to said base unit in response to said diagnostic test initiattion command.

15. The system of claim 1, wherein said base unit periodically broadcasts an electrode detection message to each of said transceiver assemblies, said transceiver assemblies responsively sending a connection confirm message to said base unit in response to said electrode detection message.

16. The system of claim 1, wherein said command comprises an audit request command, said transceiver assemblies transmitting an audit of current configuration parameters in said transceiver assembly in response to said audit request command.

17. The system of claim 1, wherein said transceiver assemblies transmit a base unit audit command to said base unit, said base unit transmitting an audit of at least one configuration parameter of said base unit in response to said base unit audit command.

18. The system of claim 1, wherein said commands comprise a data acquisition subsystem audit command, said transceiver assemblies transmitting an audit of current data acquisition subsystem configuration parameters in response to said data acquisition subsystem audit command.

19. The system of claim 1, wherein said commands comprise a set of commands establishing a registration of said transceiver assemblies with said base unit.

20. The system of claim 19, wherein said set of commands includes an assignment of an identification number of said transceiver assemblies and an assignment of a functional position of said wireless electrode on said patient.

21. The system of claim 19, wherein said set of commands further comprise an assignment of a frequency channel and a time slot to said transceiver assemblies.

22. The system of claim 19, wherein said set of commands further comprises the assignment of a base unit identification to said transceiver assembly.

23. The system of claim 1, wherein said commands comprise a set of commands establishing a signal loss recovery procedure by which said base unit may reestablish communication with one of said transceiver assemblies in the event of a total signal loss from said transceiver assembly.

24. A machine-readable storage medium containing a set of instructions executable in a base unit for over-the-air programming of a plurality of wireless transceivers, each of the said wireless transceivers adapted to couple to a sensor for connection to a patient's body, said set of instructions generating commands for remotely configuring and managing the acquisition of physiologic signals from said patient's body and transmission of said physiologic signals from said wireless transceivers to said base unit in real time either prior to or during a period in which said physiologic signals are being acquired.

25. The machine-readable storage medium of claim 24, wherein said set of instructions comprise a set of instructions illustrated in at least one of FIGS. 11–26, and wherein said wireless transceivers comprise a machine-readable storage medium containing a set of instructions for responding to the commands.

26. The machine-readable storage medium of claim 24, wherein said set of instructions prompt said base unit to generate a set of registration commands and wherein said wireless transceivers comprise a machine-readable storage medium containing a set of instructions for responding to said set of registration instructions.

27. The machine-readable storage medium of claim 24, wherein said set of instructions prompt said base unit to generate a set of signal loss recovery commands and wherein said wireless transceivers comprise a machine-readable storage medium containing a set of instructions for responding to said set of signal loss recovery commands.

28. The machine-readable storage medium of claim 24, wherein said set of instructions prompt said base unit to configure the data transmission properties of said wireless transceivers.

29. The machine-readable storage medium of claim 28, wherein said data transmission properties include selection of a carrier frequency and a time slot in a time division multiplexing communication format.

30. The machine-readable storage medium of claim 28, wherein said data transmission properties include selection of communication parameters in a CDMA communication format.

31. The machine-readable storage medium of claim 24, wherein said set of instructions include a base unit configuration routine wherein said base unit programs patient identification and position location information into said wireless transceiver assembly.

32. The machine-readable storage medium of claim 24, wherein said set of instructions include a sensor initialization routine.

33. The machine-readable storage medium of claim 24, wherein said set of instructions include a sensor activation routine.

34. The machine-readable storage medium of claim 24, wherein said set of instructions include a sensor data acquisition subsystem configuration routine.

35. The system of claim 1, wherein said wireless transceiver assemblies communicate with said base unit in a Code Division Multiple Access (CDMA) communication format.

36. In a wireless system for medical monitoring having a base unit and a least one wireless sensor for connection to a patient's body, the improvement comprising:

providing a plurality of said wireless sensors, each wireless sensor having a transceiver assembly for transmitting and receiving wireless communications with said base unit;

providing the base unit with a wireless transceiver for transmitting and receiving wireless communications with said sensors, said wireless communications including said commands, and providing a set of instructions executable in said base unit wherein said base unit may issue said commands to said transceiver assembly in response to the execution of said instructions, said transceiver assembly responding to said commands in accordance with instructions stored in said transceiver, wherein said commands from said base unit and responses to said commands from said transceiver assembly are operable to assign anatomical positions to be used by each of the wireless sensors.

37. The improvement of claim 36, wherein at least six wireless sensors are operable to be assigned to six different anatomical positions associated with ECG monitoring in response to the commands.

38. The improvement of claim 36, wherein the wireless sensors are operable to releasably connect with a disposable electrode patch.

39. The improvement of claim 36, wherein the base unit is operable to output separate analog signals corresponding to each of the wireless sensors.

* * * * *